(12) United States Patent
Montagnier

(10) Patent No.: US 10,564,118 B2
(45) Date of Patent: Feb. 18, 2020

(54) HIGHLY SENSITIVE METHOD FOR DETECTION OF VIRAL HIV DNA REMAINING AFTER ANTIRETROVIRAL THERAPY OF AIDS PATIENTS

(71) Applicant: Luc Montagnier, New York, NY (US)

(72) Inventor: Luc Montagnier, New York, NY (US)

( * ) Notice: Subject to any disclaimer, the term of this patent is extended or adjusted under 35 U.S.C. 154(b) by 287 days.

(21) Appl. No.: 15/614,416

(22) Filed: Jun. 5, 2017

(65) Prior Publication Data
US 2018/0003666 A1    Jan. 4, 2018

Related U.S. Application Data

(63) Continuation of application No. 13/731,481, filed on Dec. 31, 2012, which is a continuation of application No. 13/797,826, filed on Jun. 10, 2010.

(60) Provisional application No. 61/186,610, filed on Jun. 12, 2009.

(51) Int. Cl.
| | |
|---|---|
| *C12Q 1/68* | (2018.01) |
| *G01N 27/327* | (2006.01) |
| *C12Q 1/6806* | (2018.01) |
| *C12Q 1/6816* | (2018.01) |
| *C12Q 1/70* | (2006.01) |
| *G01N 37/00* | (2006.01) |
| *C12P 19/34* | (2006.01) |

(52) U.S. Cl.
CPC .......... *G01N 27/3275* (2013.01); *C12P 19/34* (2013.01); *C12Q 1/6806* (2013.01); *C12Q 1/6816* (2013.01); *C12Q 1/703* (2013.01); *G01N 37/005* (2013.01)

(58) Field of Classification Search
None
See application file for complete search history.

(56) References Cited

U.S. PATENT DOCUMENTS 6,274,353 B1 *  8/2001  Yang ........................ C12N 9/16
                                                        435/91.1
7,384,739 B2 *  6/2008  Kitabayashi ......... C07K 14/195
                                                        435/183

OTHER PUBLICATIONS

Zanchetta et al., Long-term decay of the HIV-1 reservoir in HIV-1-infected children treated with highly active antiretroviral therapy, J Infect Dis. Jun. 15, 2006;193(12):1718-27. Epub May 10, 2006.*
Fisher et al., Mutations proximal to the minor groove-binding track of human immunodeficiency virus type 1 reverse transcriptase differentially affect utilization of RNA versus DNA as template, J Virol. May 2003;77(10):5837-45.*

* cited by examiner

*Primary Examiner* — Aaron A Priest
(74) *Attorney, Agent, or Firm* — Tully Rinckey PLLC; Steven M. Hoffberg

(57) ABSTRACT

Methods for detecting polynucleotides, especially the DNA replicated from samples obtained from subjects infected with pathogenic viruses such as human immunodeficiency virus, by detecting electromagnetic signals ("EMS") emitted by such polynucleotides, and methods for improving the sensitivity of the polymerase chain reaction ("PCR").

19 Claims, 33 Drawing Sheets

Comparison between typical method
of PCR and improved method of PCR nested-PCR

LTR In on patient VIH+ treated with ART mixed dilutions

| NF | D2 | D3 | D4 | D5 | D6 | D7 | D8 | D9 | D10 |

Vortexed dilutions

| NF | D2 | D3 | D4 | D5 | D6 | D7 | D8 | D9 | D10 |

*Fig.9*

TABLE A

| Patient | Age | Clinical category | Treatment ARV | CV (copies/ml) | CD4/mm3 | | EMS | Positive dilutions (D) |
|---|---|---|---|---|---|---|---|---|
| B1 | 40 | Asymptomatic untreated | | 180000 | 416 | plasma | – | |
| | | | | | | plasma DNA | – | |
| | | | | | | WBC DNA | – | |
| | | | | | | RBC DNA | – | |
| B2 | 57 | Asymptomatic untreated | | ND | 338 | plasma | – | |
| | | | | | | plasma DNA | – | |
| | | | | | | WBC DNA | – | |
| | | | | | | RBC DNA | – | |
| B3 | 22 | Asymptomatic untreated | | ND | 509 | plasma DNA | – | |
| B4 | 58 | Asymptomatic untreated | | ND | 221 | plasma DNA | – | |

*Fig. 10A*

| C1 | 33 | Symptomatic treated | TDF+FTC+EFV | <200 | | plasma | + | D4 to D7 |
|---|---|---|---|---|---|---|---|---|
| | | | | | 520 | plasma DNA | + | D4 to D8 |
| | | | | | | WBC DNA | − | |
| | | | | | | RBC DNA | + | D5 to D9 |
| C2 | 45 | Symptomatic treated | AZT+3TC+EFV | <200 | | plasma | + | D5 to D9 |
| | | | | | 381 | plasma DNA | + | D5 to D9 |
| | | | | | | WBC DNA | − | |
| | | | | | | RBC DNA | + | D5 to D8 |
| C3 | 44 | Symptomatic treated | AZT+3TC+EFV | <200 | | plasma | + | D6 to D9 |
| | | | | | 289 | plasma DNA | + | D3 to D7 |
| | | | | | | WBC DNA | − | |
| | | | | | | RBC DNA | + | D4 to D8 |

*Fig. 10B*

| | | AZT+3TC+EFV | <40 | 258 | plasma | ND | |
|---|---|---|---|---|---|---|---|
| C4 | 51 | Symptomatic treated | | | plasma DNA | + | D5 to D9 |
| | | | | | WBC DNA | ND | |
| | | | | | RBC DNA | + | D5 to D8 |
| D1 | 39 | Symptomatic, not yet treated | ND | 93 | plasma | – | |
| | | | | | plasma DNA | – | |
| | | | | | WBC DNA | – | |
| | | | | | RBC DNA | – | |
| D2 | 32 | Symptomatic, not yet treated | ND | 162 | plasma DNA | – | |
| D3 | 27 | Symptomatic, not yet treated | ND | 153 | plasma DNA | – | |
| D4 | 55 | Symptomatic, not yet treated | ND | 27 | plasma DNA | – | |

Legend for Table A: Detection of EMS from VIH DNA of AIDS patients treated with ART. [ND: Not done; RBC: Red Blood Cells; WBC: White Blood Cells; 3TC: Epivir® (Lamiduvine); FTC: Emtrive® (Emtricitabine); TDF: Viréal® (Tenofovir); AZT: Rétrovir® (Zidovudine); EFV: Sustiva® (Efavirenz); EMS: Electromagnetic signals]

*Fig. 10C*

TABLE B

| HIV GENES | | Sequence range | N° of base pair (bp) | DNA | EMS | Positive dilutions (D) |
|---|---|---|---|---|---|---|
| GAG | PCR | 890 → 2278 | 1388 | Clone | − | |
| | n−PCR | 1491 → 2038 | 547 | Patient (C1) | ND | |
| | | | | Clone | − | |
| POL | PCR | 3219 → 4805 | 1586 | Patient (C1) | ND | |
| | n−PCR | 4174 → 4669 | 495 | Clone | − | |
| | | | | Patient (C1) | ND | |
| ENV | PCR | 6438 → 7816 | 1378 | Clone | − | |
| | n−PCR | 6848 → 7521 | 673 | Patient (C1) | ND | |
| | | | | Clone | + | D4 to D8 |
| | | | | Patient (C1) | ND | |

Fig.11A

| LTR | PCR | 83 → 570 | 487 | Clone | − | |
| | | | | Patient (C1) | − | |
| | n-PCR | 445 → 549 | 104 | Clone | + | D4 to D8 |
| | | | | Patient (C1) | + | D4 to D8 |
| NEF | PCR | 8797 → 9398 | 601 | Clone | − | |
| | | | | Patient (C1) | − | |
| | n-PCR | 9066 → 9280 | 214 | Clone | + | D5 to D9 |
| | | | | Patient | + | D4 to D7 |

*Fig.11B*

Legend for Table B: Detection of EMS from DNA bands resulting from PCR and n-PCR [ND: not done; PCR: Polymerase Chain Reaction; n-PCR: nested PCR; EMS: Electromagnetic signals; D: dilution factor]

HIGHLY SENSITIVE METHOD FOR DETECTION OF VIRAL HIV DNA REMAINING AFTER ANTIRETROVIRAL THERAPY OF AIDS PATIENTS

CROSS-REFERENCE TO RELATED APPLICATION(S)

This application is a Continuation of U.S. patent application Ser. No. 13/831,481, filed Dec. 31, 2012, now pending, which claims priority under 35 U.S.C. § 120 to U.S. Ser. No. 12/797,826, filed Jun. 10, 2010, now abandoned, which claims priority under 35 U.S.C. § 119(e) to U.S. Provisional 61/186,610, filed Jun. 12, 2009, each of which is incorporated by reference in its entirety.

BACKGROUND OF THE INVENTION

1. Field of the Invention

Methods for detecting polynucleotides, especially the DNA replicated from samples obtained from subjects infected with pathogenic viruses such as human immunodeficiency virus, by detecting electromagnetic signals ("EMS") emitted by such polynucleotides, and methods for improving the sensitivity of the polymerase chain reaction ("PCR").

Electromagnetic signals of low frequency have been shown to be produced in aqueous dilutions by Human Immunodeficiency Virus DNA. In vivo, HIV DNA signals are detected only in patients previously treated by antiretroviral therapy and having no detectable viral RNA copies in their blood. It is suggested that the treatment of AIDS patients pushes the virus towards a new mode of replication implying only DNA, thus forming a reservoir insensitive to retroviral inhibitors. Implications for new approaches aimed at eradicating HIV infection are disclosed.

2. Description of the Related Art

Antiretroviral therapy (ART) is now the standard treatment of HIV infected patients. Generally composed of three or four inhibitors of the viral reverse transcriptase and protease, it results in a quasi-complete disappearance of HIV viremia, or measured by the strong reduction of viral RNA copies (viral load) in the patient's serum. The limit of detection of RNA copies by commercial kits (200 virus/ml or 40 virus/ml) is usually attained within 3 to 6 months when the virus is fully sensitive to the viral inhibitors. However, as soon as the treatment is interrupted, virus multiplication resumes within weeks, as evidenced by the increase of the virus load and the decrease of the CD4 T-cell numbers.

This indicates that there is a viral reservoir to which the inhibitors have no access or no effect. This reservoir is presumably made of proviral DNA integrated in cells in a dormant state. It is shown that ART treatment of patients induces the release into their blood of HIV DNA sequences detectable by a new biophysical technology. The data suggests that inhibition of infection at the reverse transcription step is pushing the virus towards a low level of replication using only DNA templates. This would explain why the classical inhibitors used in ART cannot achieve eradication of the viral infection.

Detection of electromagnetic waves of low frequency by high dilutions in water of the DNA of pathogenic bacteria has been previously reported. This is a resonance phenomenon likely to be produced by polymerized water molecules organized by some DNA sequences. It has been contemplated that the genetic material of viruses, particularly that of HIV, could also induce the same transformation of water.

Pathogenic microorganisms in this day of age are not only submitted to high selective pressure by the immune defenses of their hosts but also have to survive under highly active antiviral treatments. Not surprisingly, they have evolved in finding many ways to escape these hostile conditions, such as mutations of resistance, hypervariability of surface antigens, protective biofilms, latency inside cells and tissues. It has been observed that some filtration procedures aimed at sterilizing biological fluids can yield under some defined conditions the infectious microorganism which was present before the filtration step. A 20 nM filtration did not retain a minor infective fraction of HIV, the causal agent of AIDS, whose viral particles have a diameter averaging 100-120 nM. In the course of investigating the nature of such filtering infectious forms, another property of the filtrates was found that may or may not be related to the former: their capacity to produce some electromagnetic waves of low frequency in a reproducible manner after appropriate dilutions in water.

The emission of such waves is likely to represent a resonance phenomenon depending on excitation by the ambient electromagnetic noise. It is associated with the presence in the aqueous dilutions of polymeric nanostructures of defined size. The supernatant of uninfected eukaryotic cells used as controls did not exhibit this property. Disclosed is a first characterization of the electromagnetic signals (EMS) and of their underlying nanostructures produced by some purified viruses.

BRIEF SUMMARY OF THE INVENTION

The disclosed invention includes:

A method of detecting electromagnetic signals (EMS) emitted by genes of viruses, in particular genes from pathogenic viruses. Also, a method of detecting electromagnetic signals emitted by DNA or specific nucleotide sequences. The methods include steps of filtering, diluting, and vortexing of samples of body fluids, tissues or cells; or samples of DNA extracted from body fluids, tissues or cells. The samples are serially diluted with the samples being vigorously vortexed between each dilution step.

A method of improving the sensitivity of PCR by 10 to 100 times by processing samples with serial dilutions (1/10 at each step) and vigorous vortexing between each dilution step. Additionally, RNase treatment of the filtered original sample can be combined with the serial dilution process.

A composition of viral genes, specific nucleotide sequences or DNA, in general, that is able to emit EMS when the appropriate dilution of the sample is obtained by serial dilution and vortexing between each dilution step.

A machine to process biological samples to automatically make the initial solution of biological fluid or solution of DNA extracted from a biological sample of body fluid, tissue or cells; filter the original solution followed by serial dilutions of the sample with vortexing of the diluted sample before the next serial dilution; and detecting, measuring and analyzing an emitted EMS to determine if it corresponds to an EMS from a specific pathogenic virus or gene.

A machine to detect a pathogenic infection in a human or animal by a non-invasive method and detecting, measuring and analyzing an emitted EMS from a body part placed on a scanner surface. The detected EMS would be compared to an EMS indicative of the specific pathogenic infection.

Additional embodiments of the disclosed invention are described below.

BRIEF DESCRIPTION OF THE DRAWINGS

EMS in "Silent" and "Loud" Samples

FIG. 1A shows an EMS with large changes in the amplitude of the signal with small changes in frequency and small ranges between the high and low values.

FIG. 1A shows a very different signal pattern. The amplitude of the signal remains relatively constant with a higher frequency of spikes and a large range between the high and low value of each spike. FIG. 1B shows that the spikes are very large on the right side of the graphs. FIG. 1C now shows large spikes near the origin with large spikes found all along the base of the graph.

Stability of EMS in Sample

Figure 1A:
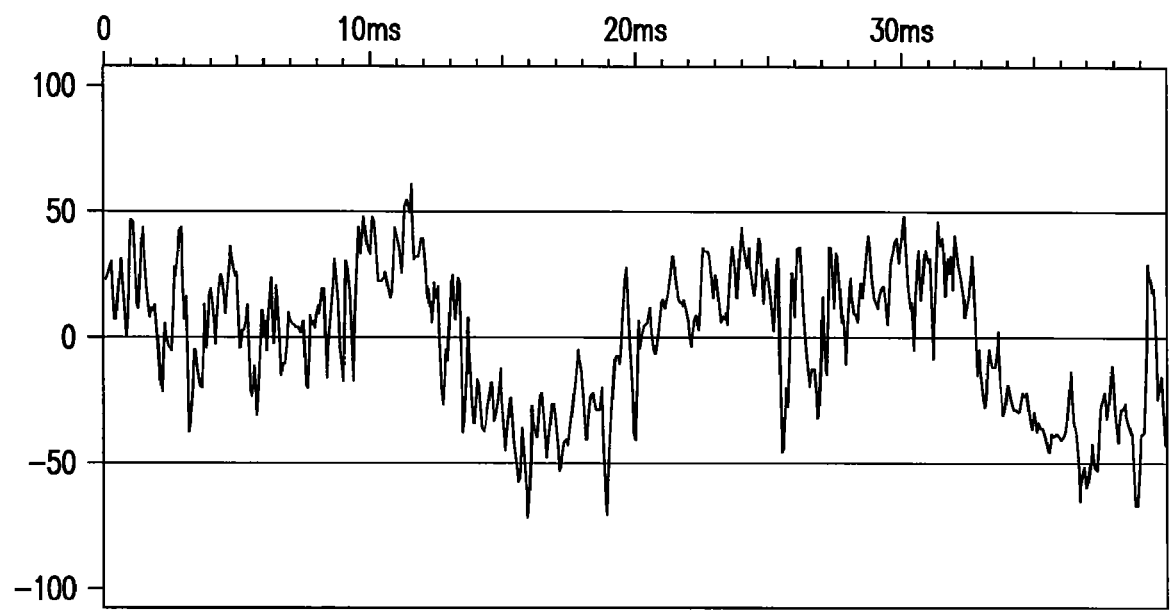
FIGS. 1A, B and C show a typical background EMS detected in an unfiltered suspension or a negative low dilution, and how this background noise appears after it has been analyzed with Fourier transformation, graphic representation, and harmonics.
Figure 1B:
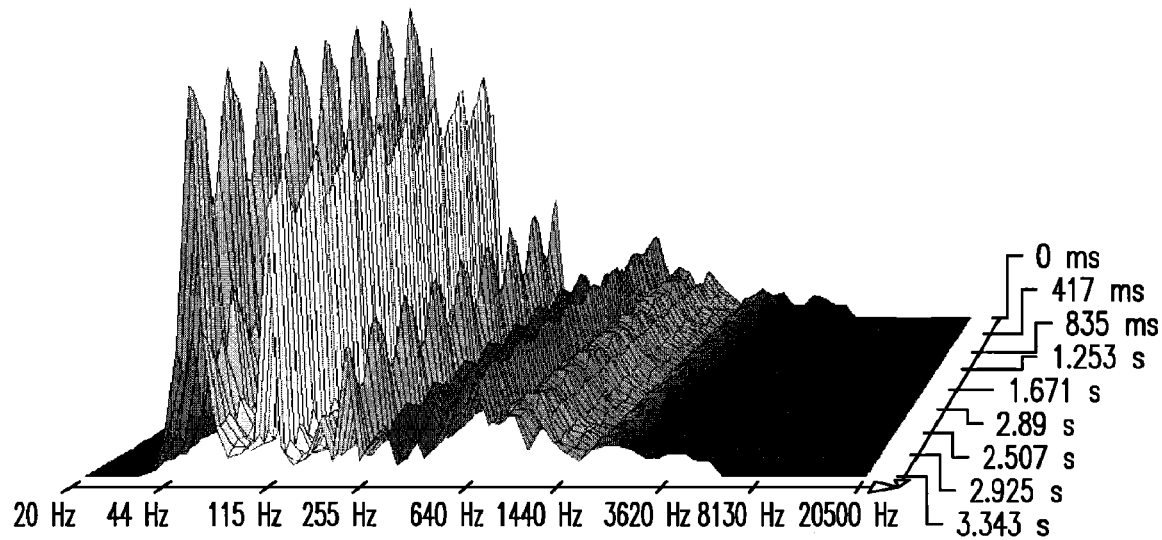
FIG. 1B shows that the spikes are very small on the right side of the graph.
Figure 1C:
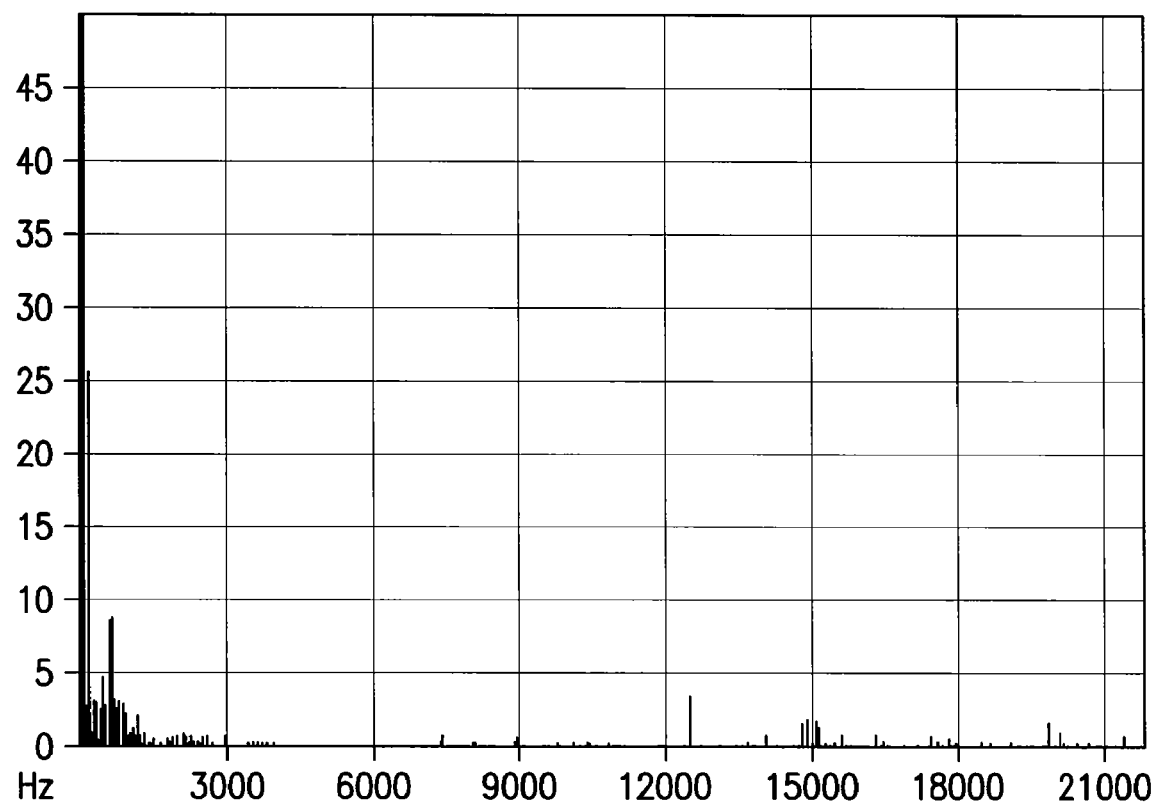
FIG. 1C shows only small peaks near the origin and spaced along the graph.
Figure 2A:
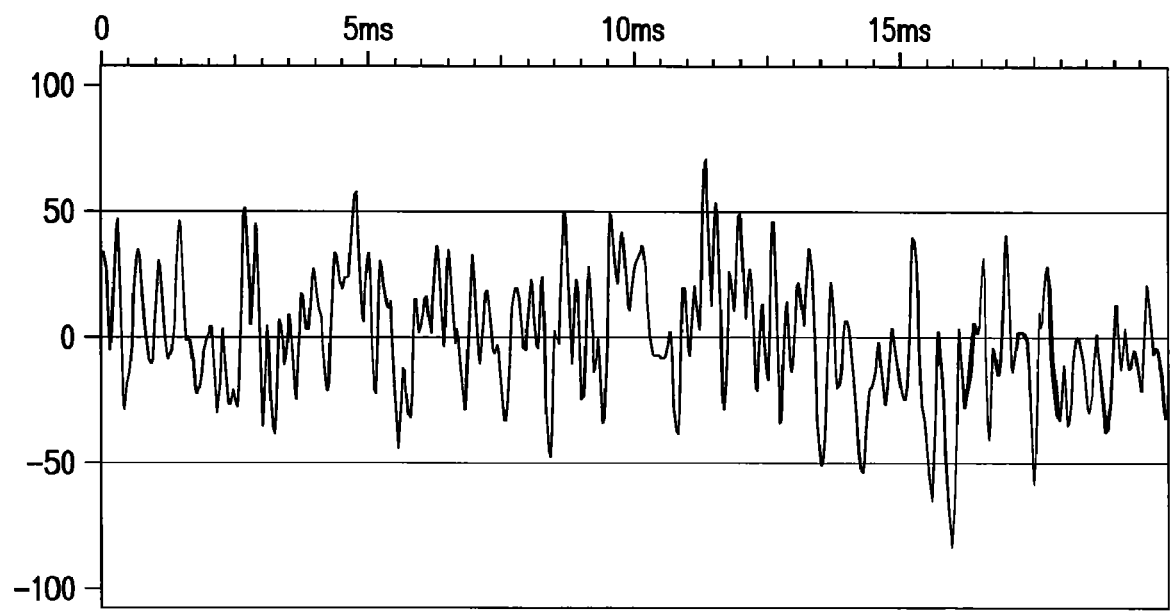
FIGS. 2 A, B and C show a typical EMS recording from the plasma DNA of a patient positive for HIV and who has received antiretroviral therapy.
Figure 2B:
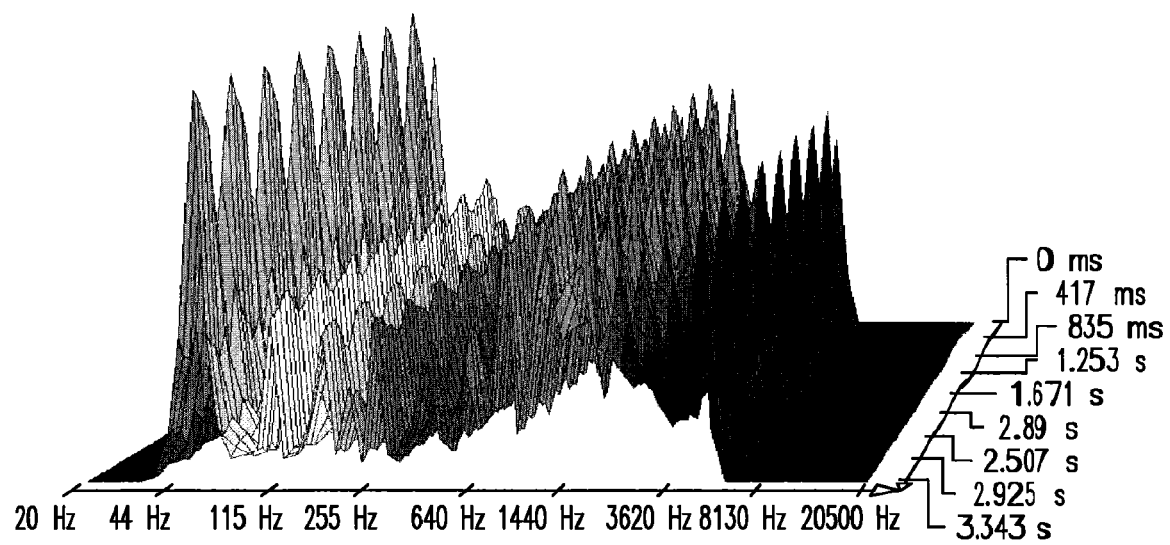
Figure 2C:
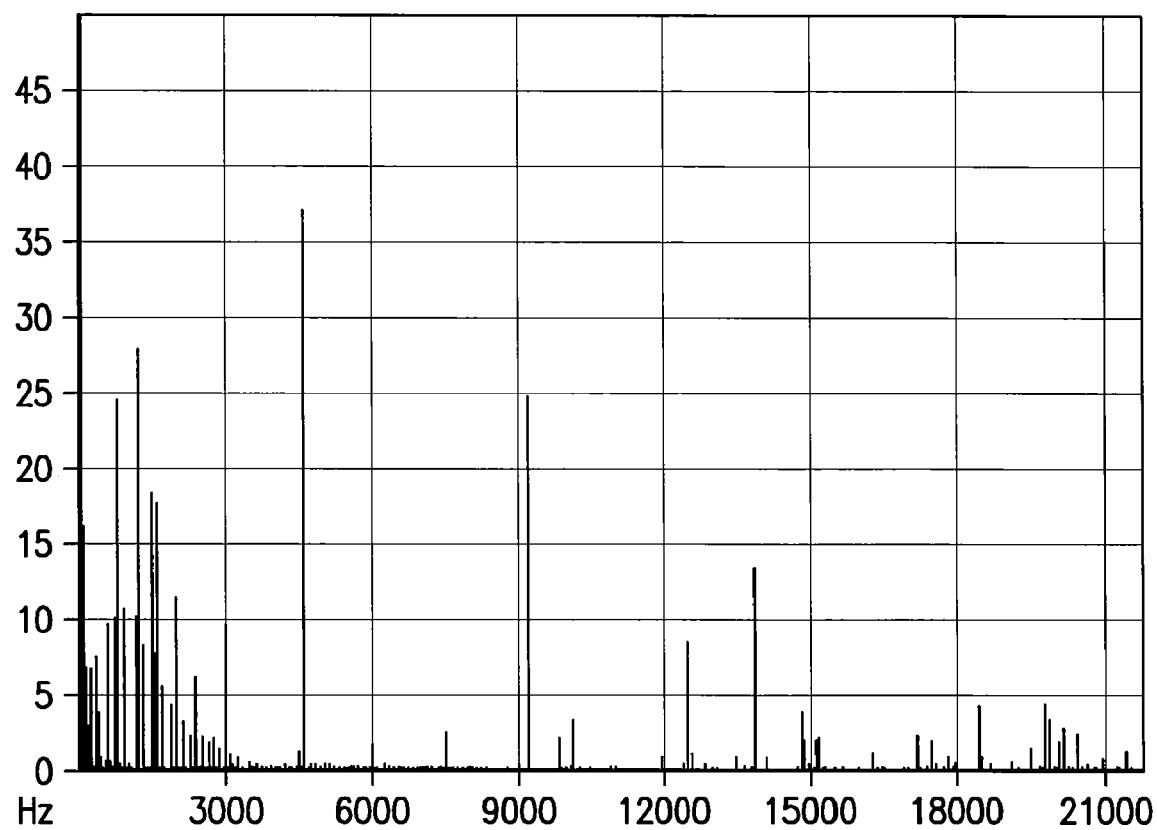
Figure 3A:
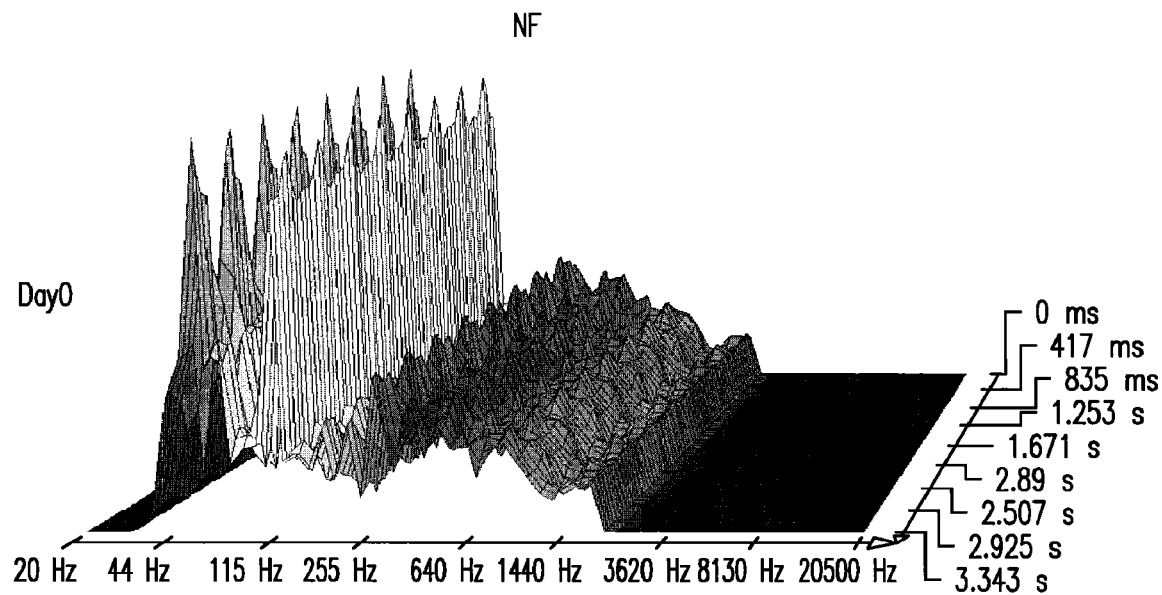
Figure 3B:
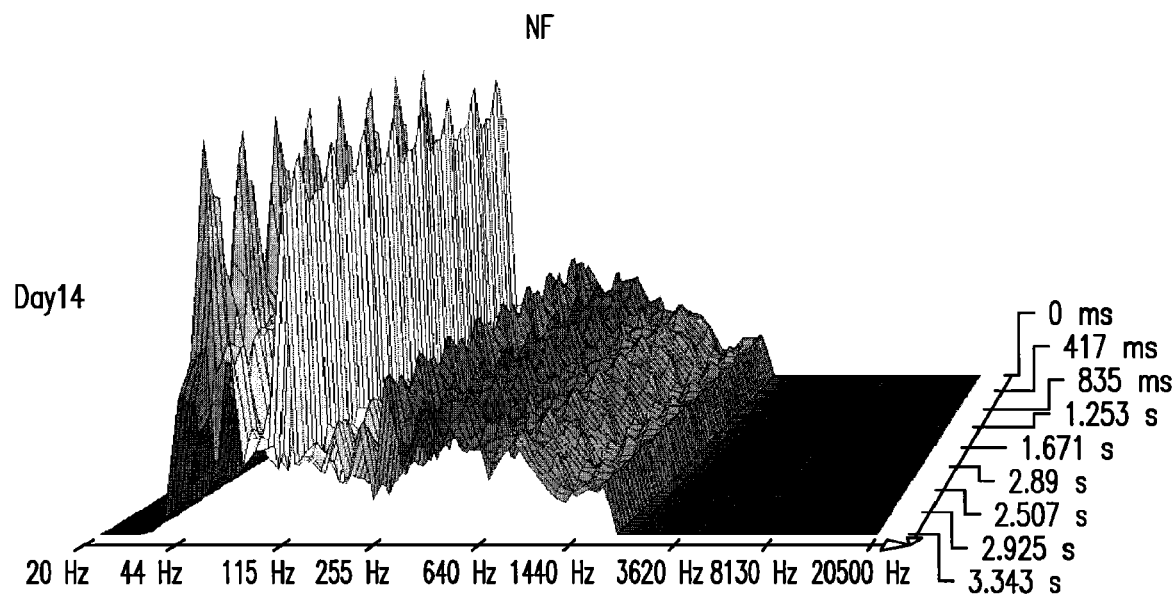
Figure 3C:
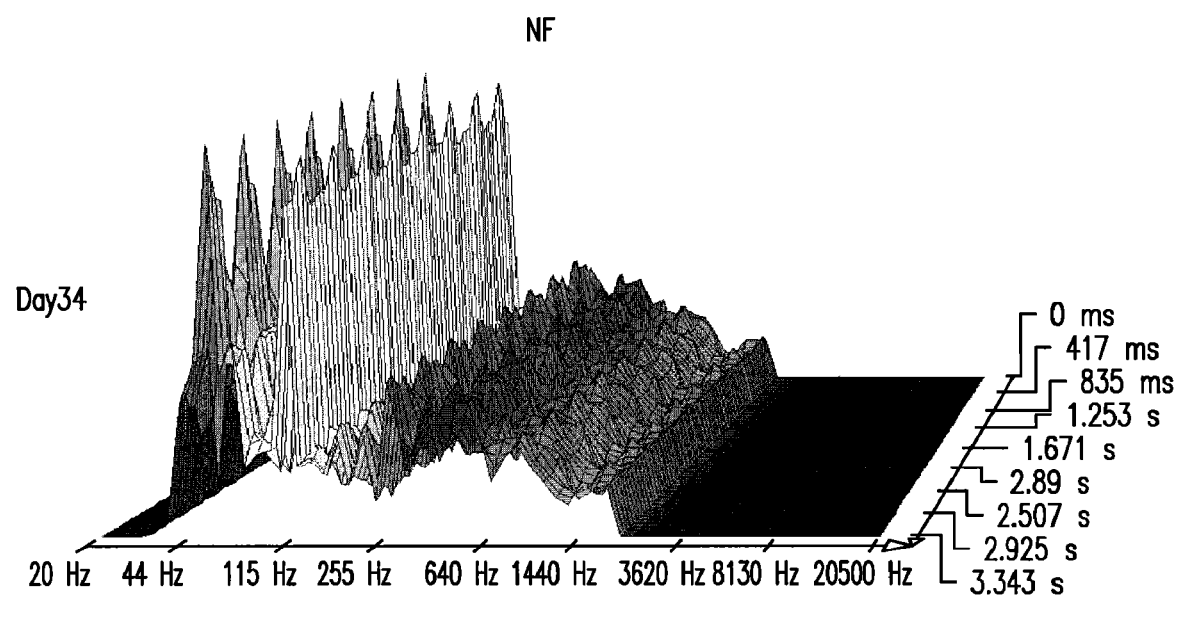

FIGS. 3A, B and C show the EMS emission from a sample of plasma from a patient positive for HIV and who has received antiretroviral therapy. The sample has been stored at C. The EMS recording on Day 0 in FIG. 3A has the typical appearance of only having background EMS with the right side of the graph having small spikes. When the same sample has the EMS recorded on Day 14 (FIG. 3B) and Day 34 (FIG. 3C), there is no change in the EMS and it looks just like the recording taken on Day 0 (FIG. 3A).

Figure 4A:
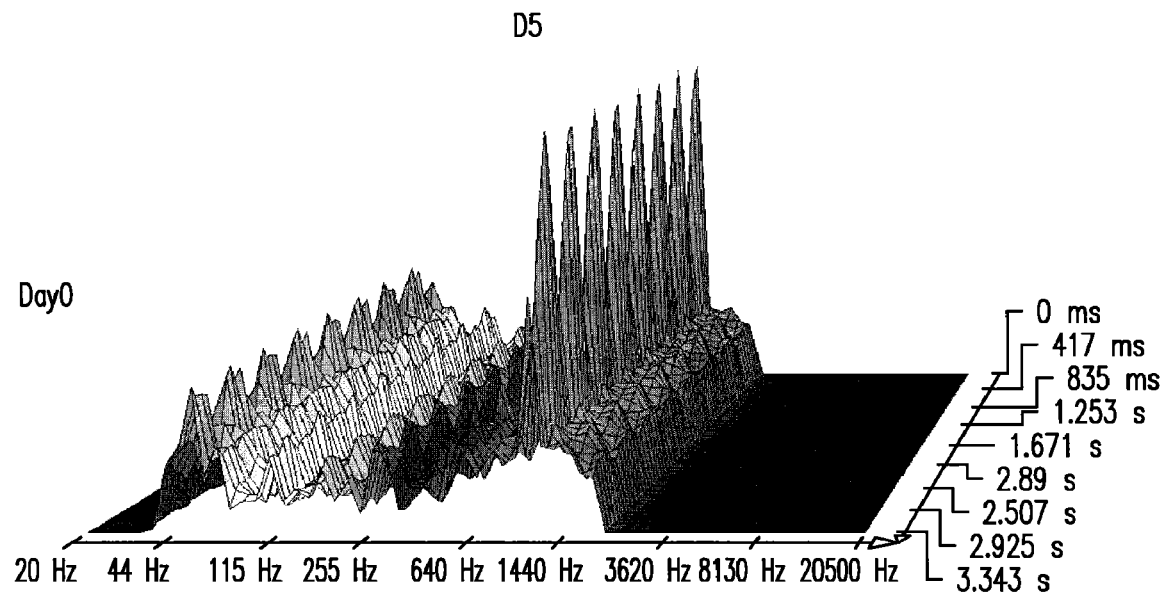
Figure 4B:
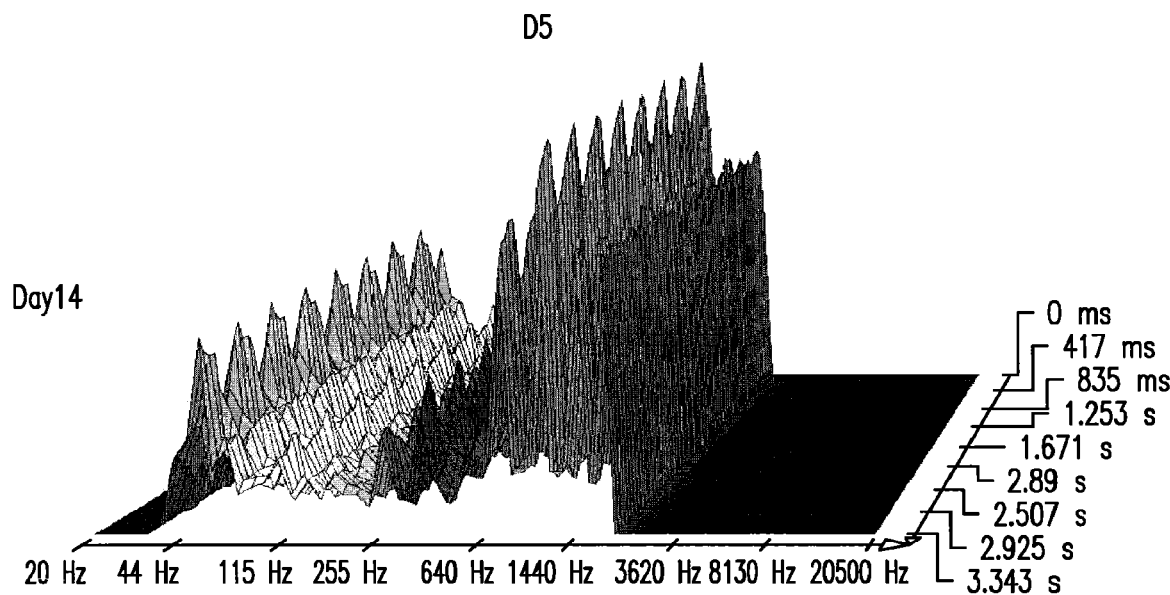
Figure 4C:
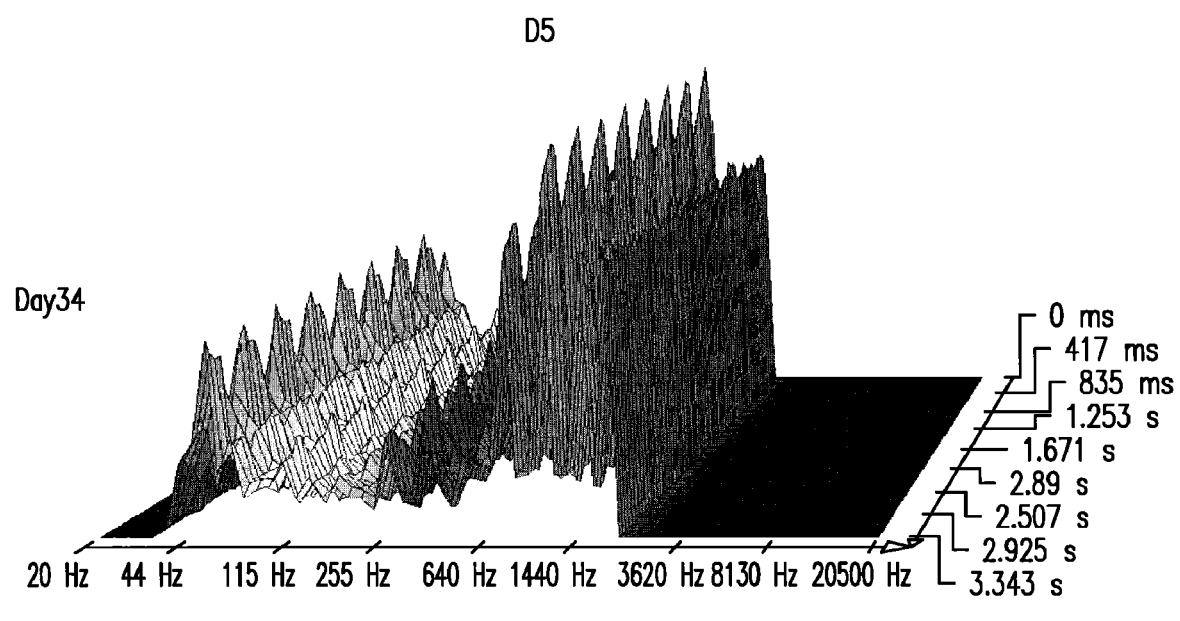

FIGS. 4A, B and C show the EMS emission from a sample of plasma from a patient positive for HIV and who has received antiretroviral therapy. The sample has been stored at C; however it has been filtered and diluted to $10^{-5}$ in serial steps of 1 part sample solution:9 parts diluent (decimal dilution) with each step consisting of dilution followed by vigorous and sustained vortexing of the prepared diluted solution. The sample was diluted in steps from the original sample to $10^{-1}$, $10^{-2}$, $10^{-3}$, $10^{-4}$, and finally to $10^{-5}$. The EMS was recorded from the $10^{-5}$ dilution. The EMS recorded on Day 0 (FIG. 4A) has very large peaks on the right side of the graph as compared to the peaks on the left side of the graph. The EMS recorded on Day 14 (FIG. 4B) still has large peaks with the range of the peaks expanded a little more compared to the recording on Day 0 (FIG. 4A). The EMS recording on Day 34 (FIG. 4C) is very similar to Day 14 and still shows the typical pattern seen in a sample emitting an EMS from the HIV virus. The stability of the EMS generating entity appears to persist for many days and weeks in some samples.

EMS Signal Versus Dilution of the Sample

Figure 5A:
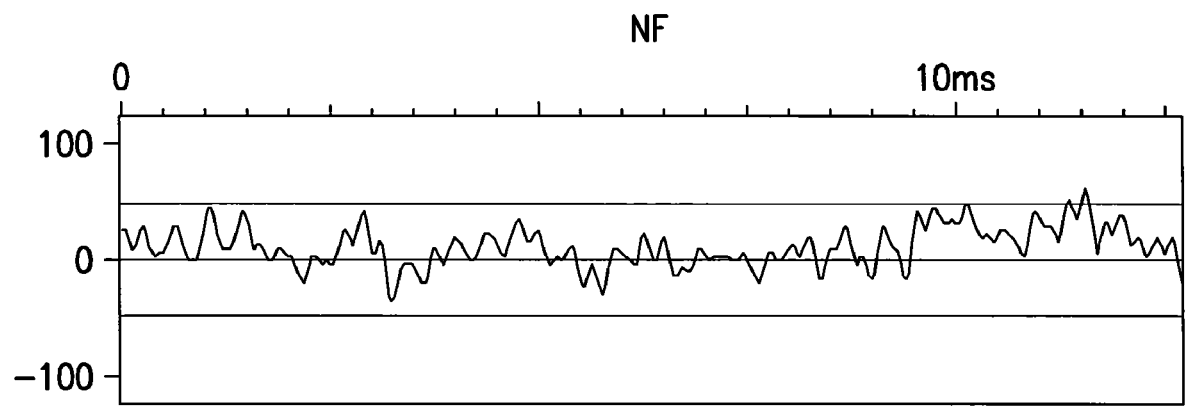
Figure 5B:
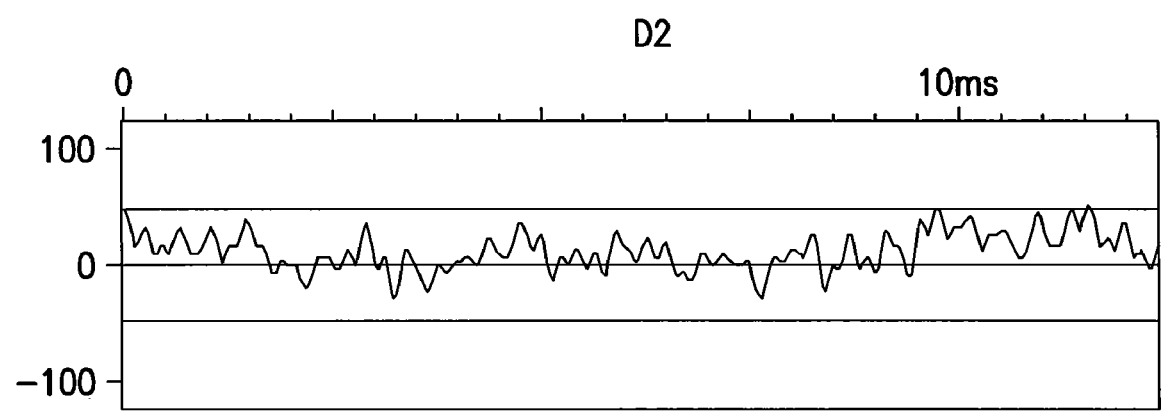
Figure 5C:
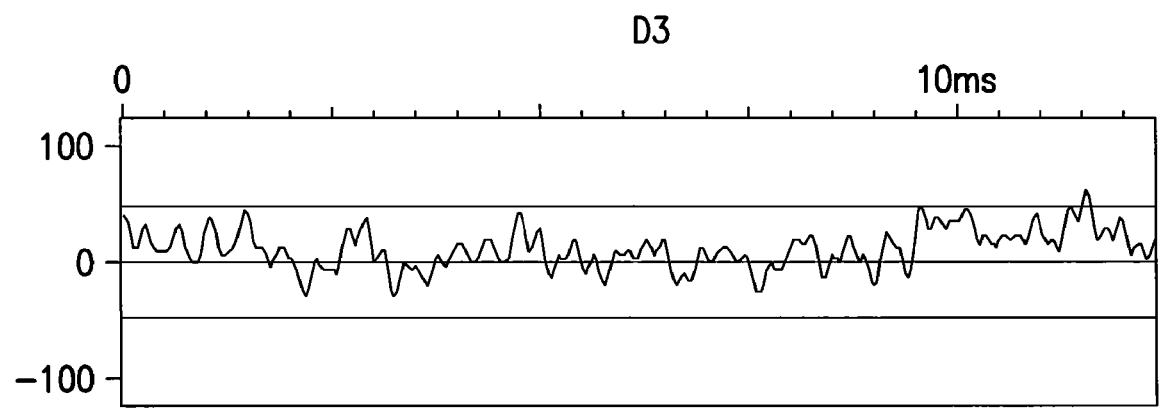
Figure 5D:
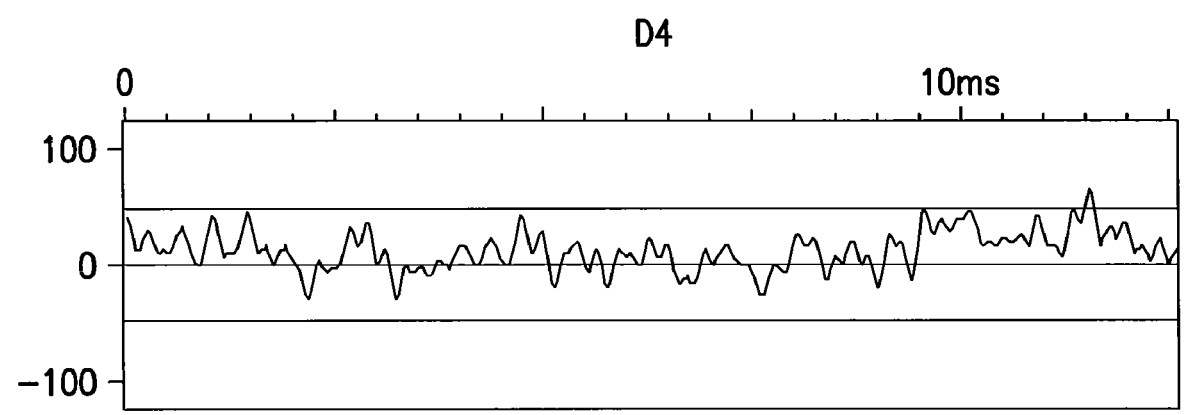
Figure 5E:
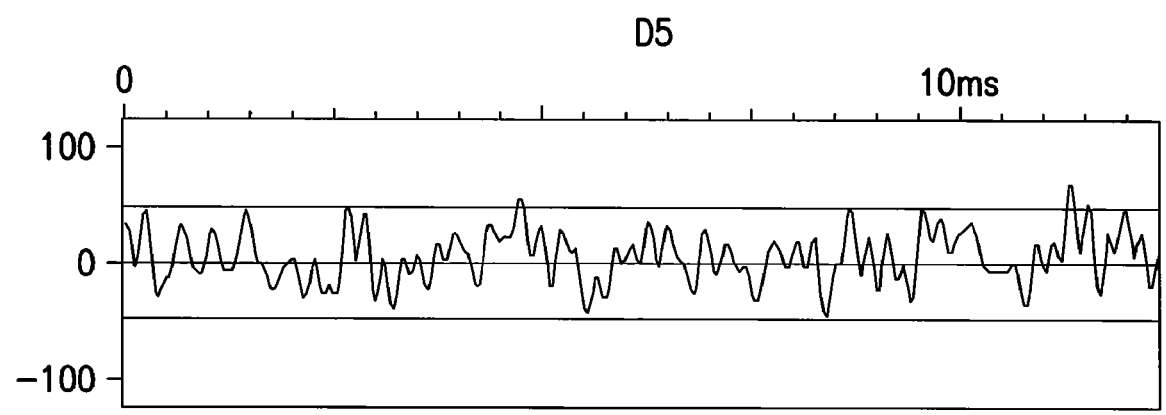
Figure 5F:
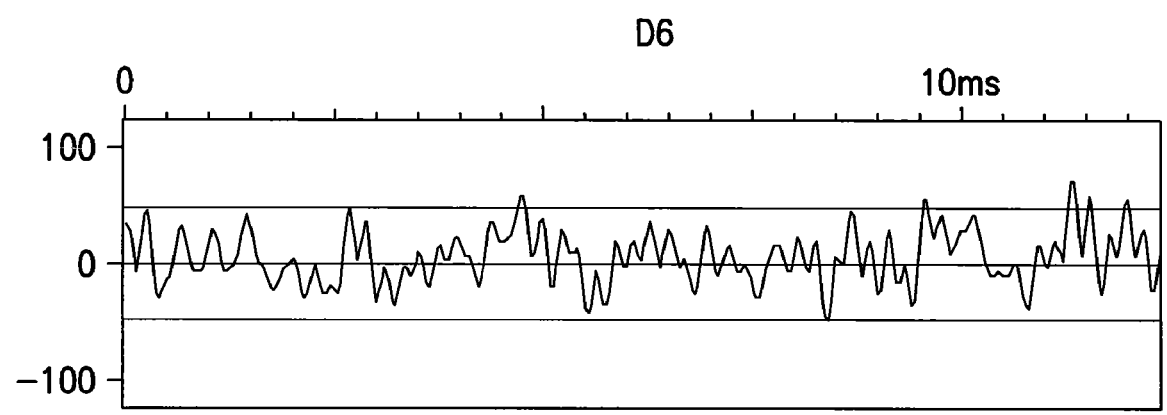
Figure 5G:
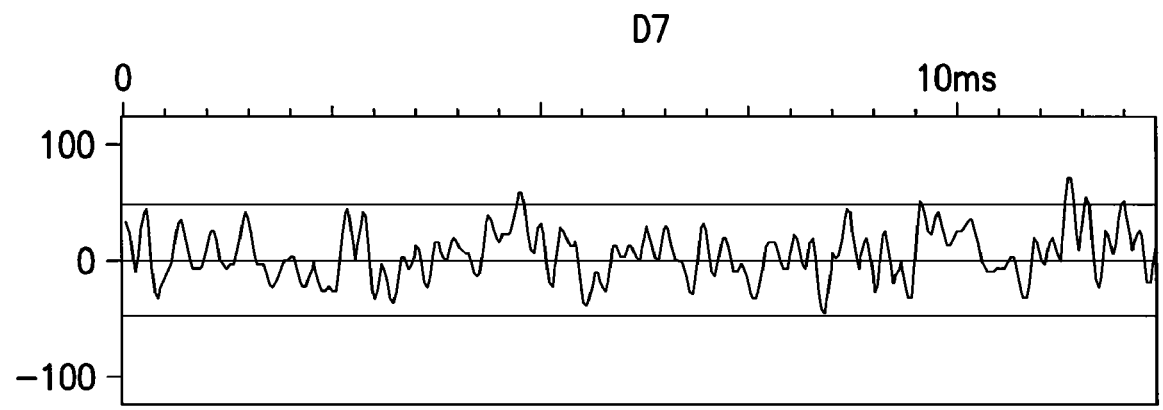
Figure 5H:
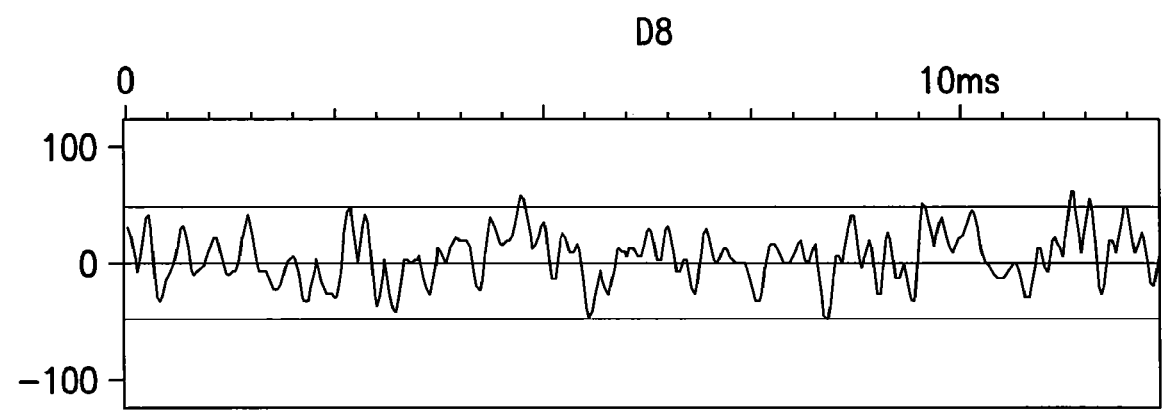
Figure 5I:
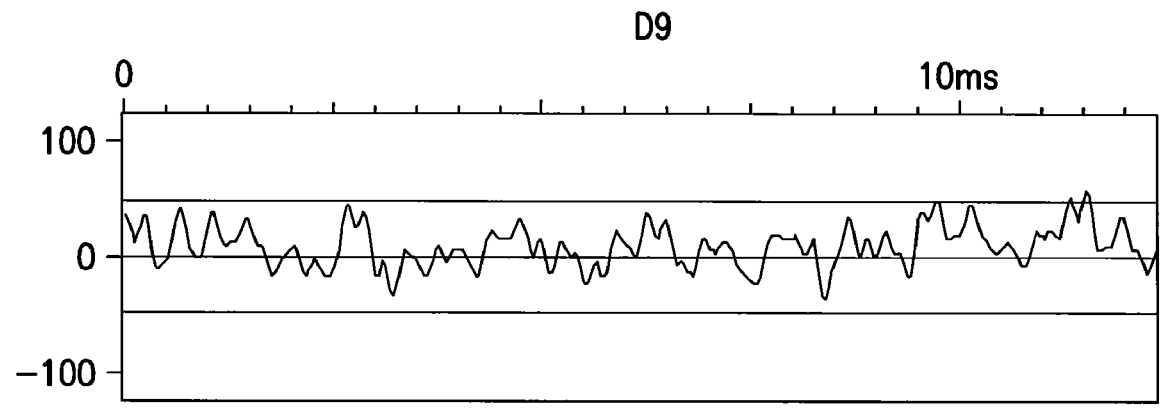
Figure 5J:
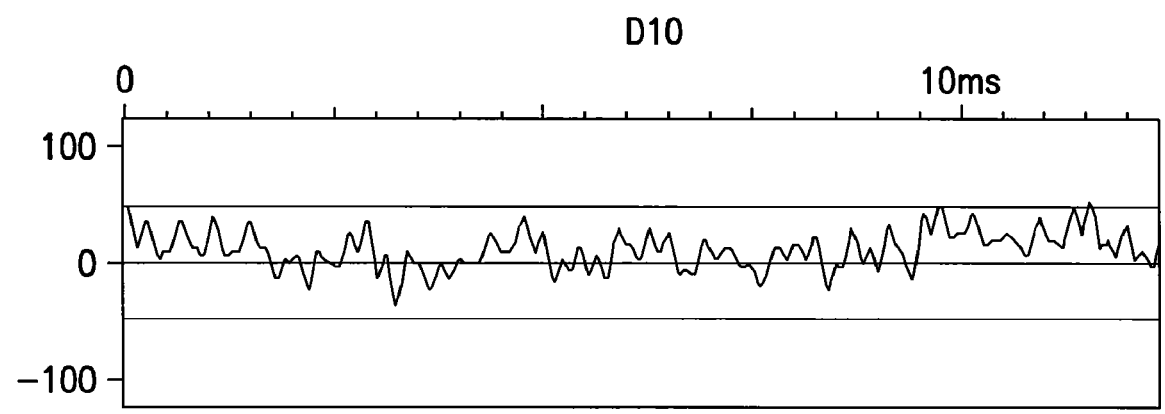
Figure 5K:
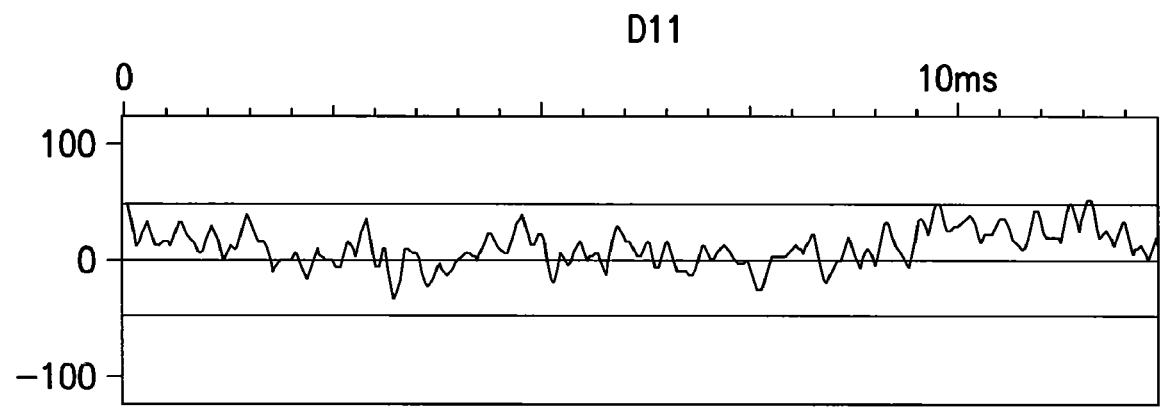
Figure 5L:
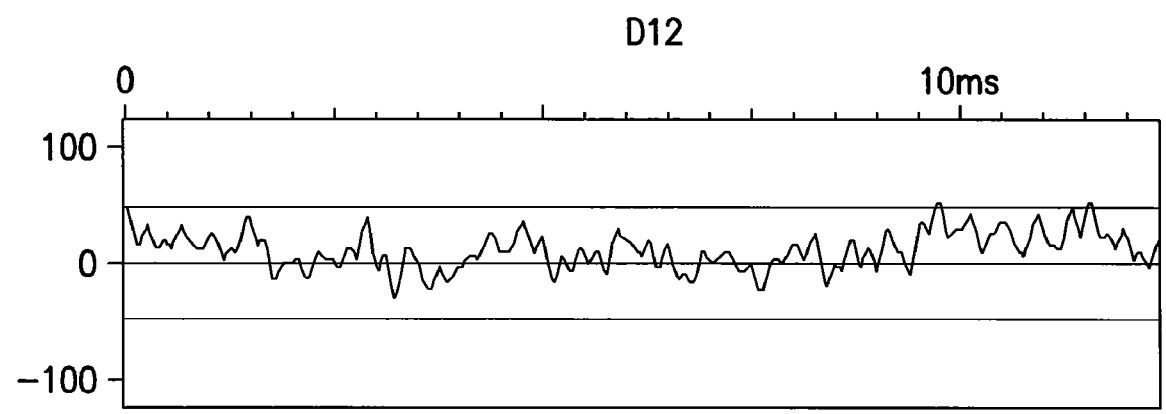

FIGS. 5A, B, C, D, E, F, G, H, I, J, K and L show the EMS recording from the serial dilutions of a sample of plasma DNA from a patient positive for HIV and who has received antiretroviral therapy. EMS recordings were taken from each serial dilution from beginning with the original not filtered (NF) sample (FIG. 5A) through the first dilution of $10^{-1}$ (FIG. 5B) through the intervening serial dilutions described by FIGS. 5C, 5D, 5E, 5F, 5G, 5H, 5J, and 5K to the last dilution of $10^{-12}$ (FIG. 5L). Also, it must be noted that each serial dilution was vigorously vortexed before making the next dilution in series. The EMS signal in the non-filtered sample has the appearance of background noise with none of the typical changes in the signal pattern seen in an EMS emitting sample. Sample D5 ($10^{-5}$ dilution) (FIG. 5E) begins to show the typical pattern of an EMS emitting sample and this pattern continues in the samples until D8 ($10^{-8}$) (FIG. 5H). Sample D9 ($10^{-9}$) (FIG. 5I) shows that the EMS pattern has reverted back to that seen in the non-filtered sample that is typical of background noise. This pattern continues in the samples up to D12 ($10^{-12}$) (FIG. 5L). These graphs show that low dilutions and very high dilutions do not emit EMS. It is only the dilutions in the range of $10^{-5}$ to $10^{-8}$ that have the detectable EMS.

Figure 6A:
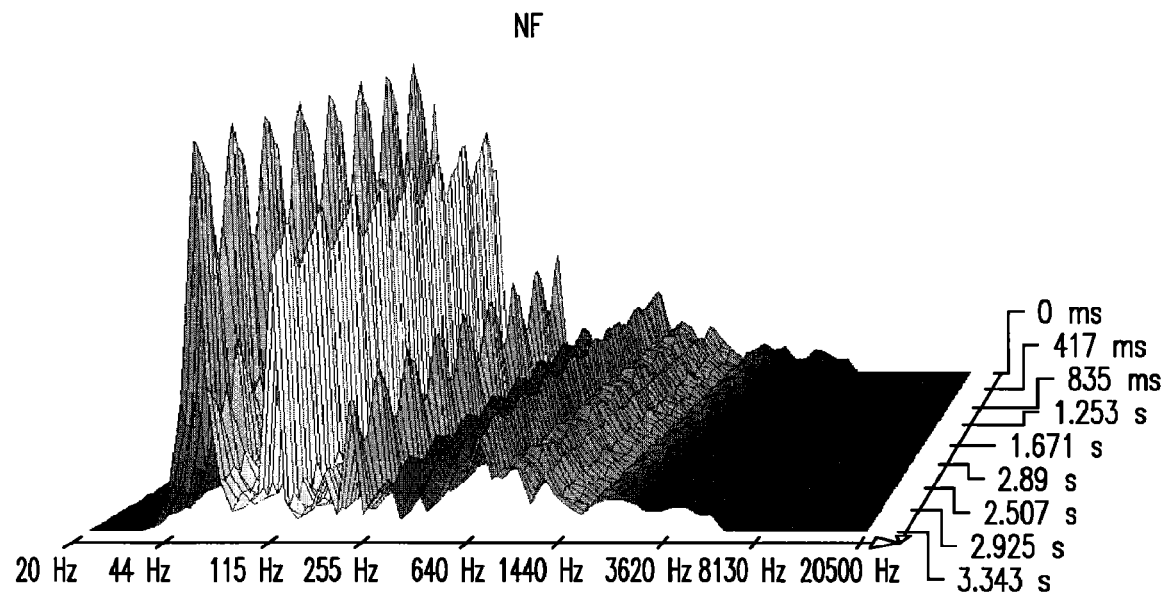
Figure 6B:
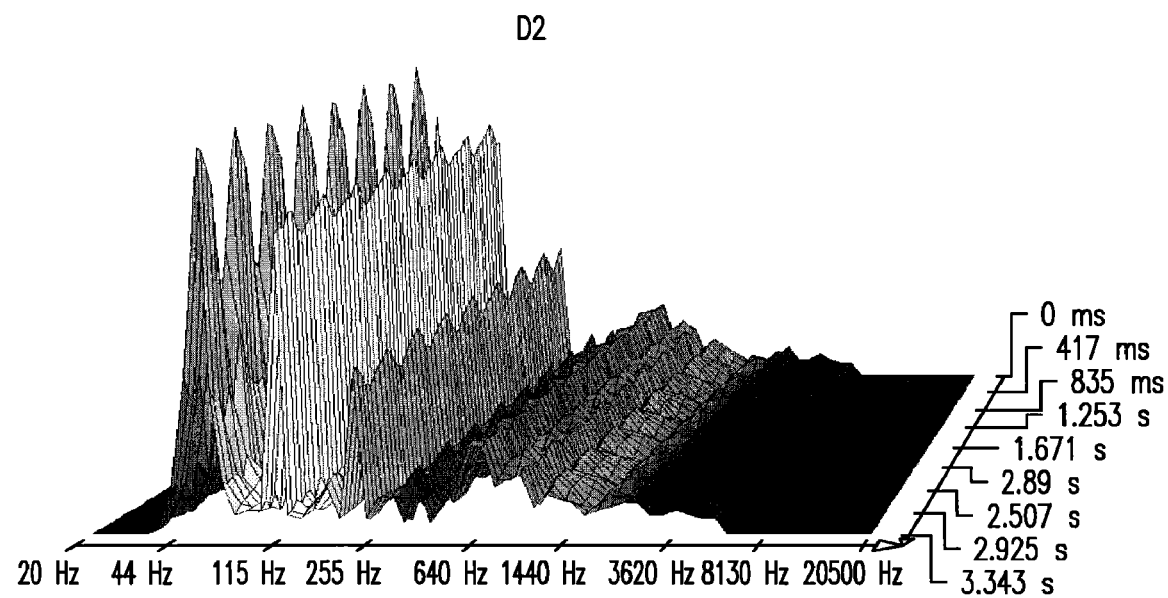
Figure 6C:
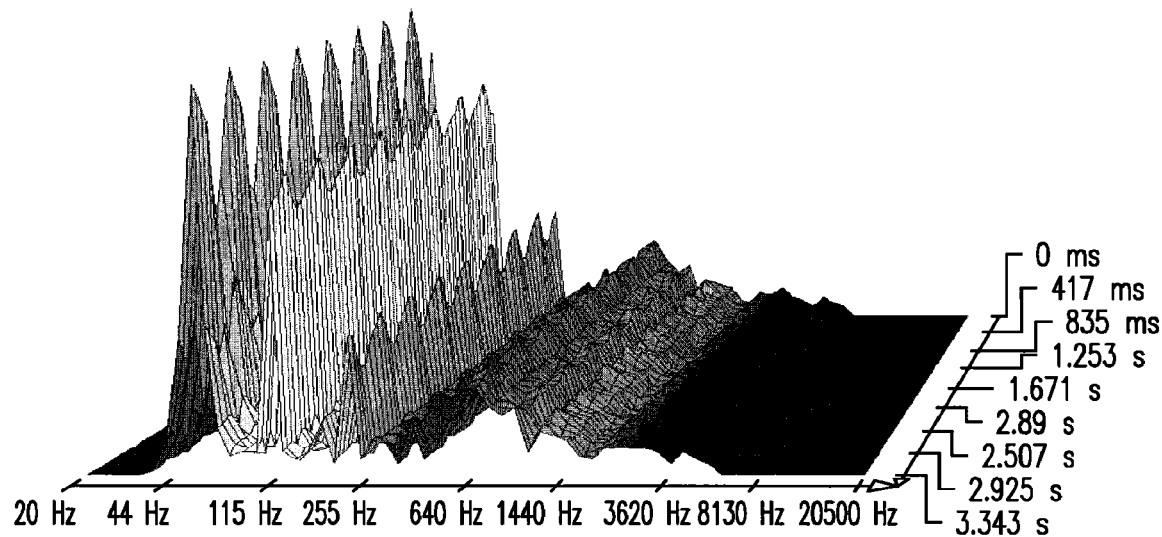
Figure 6D:
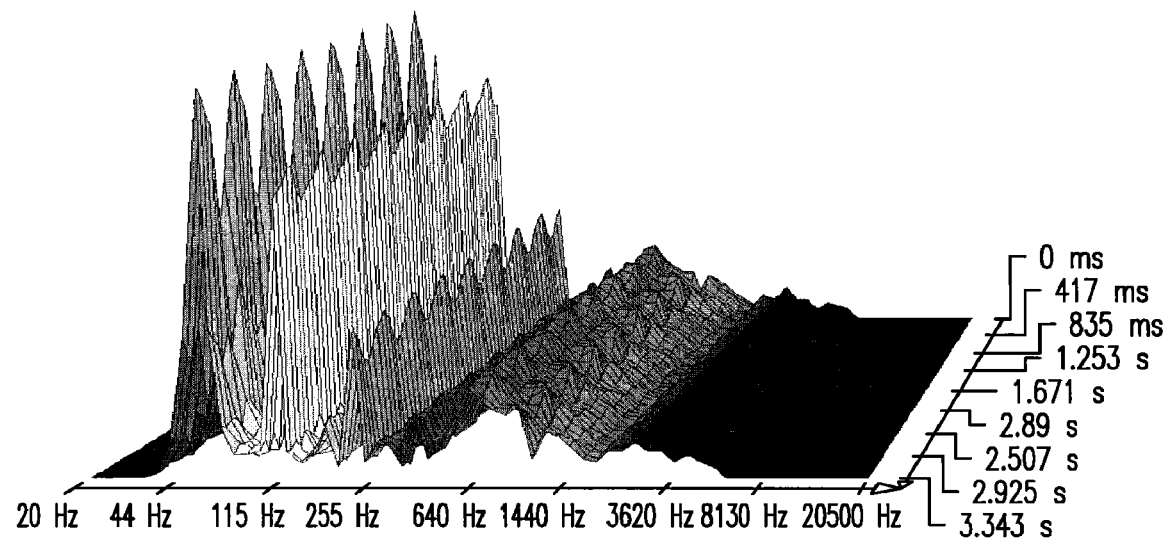
Figure 6E:
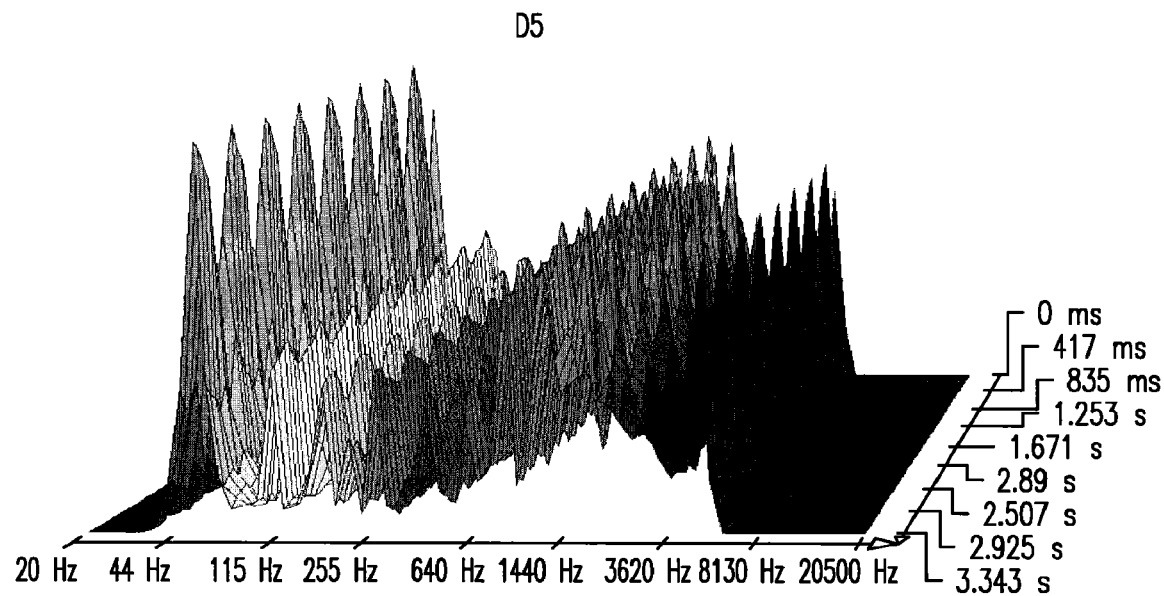
Figure 6F:
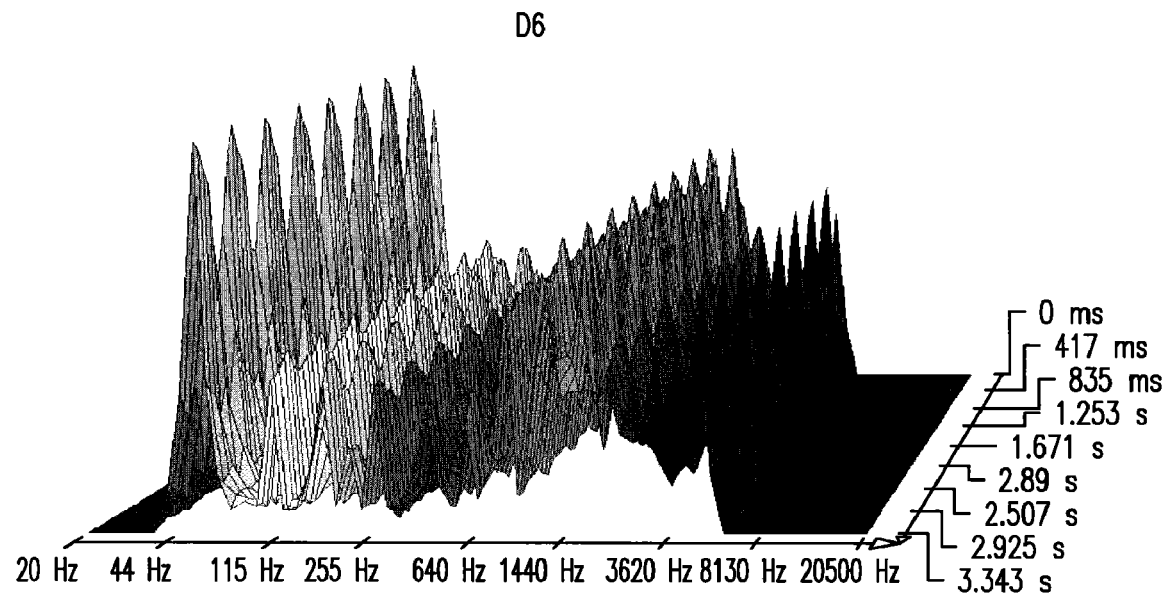
Figure 6G:
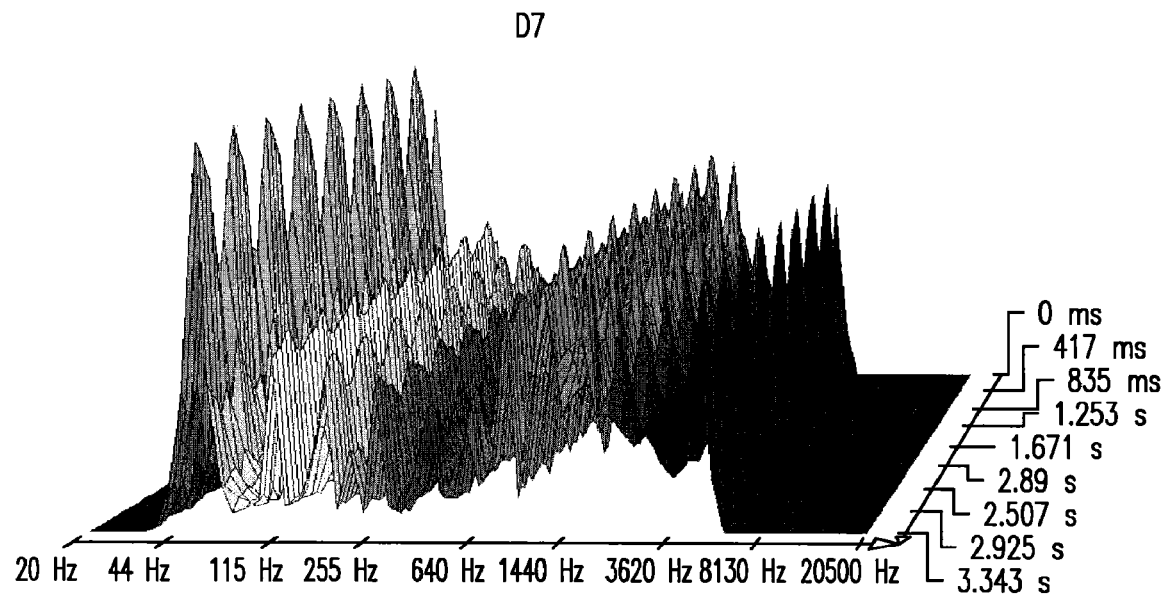
Figure 6H:
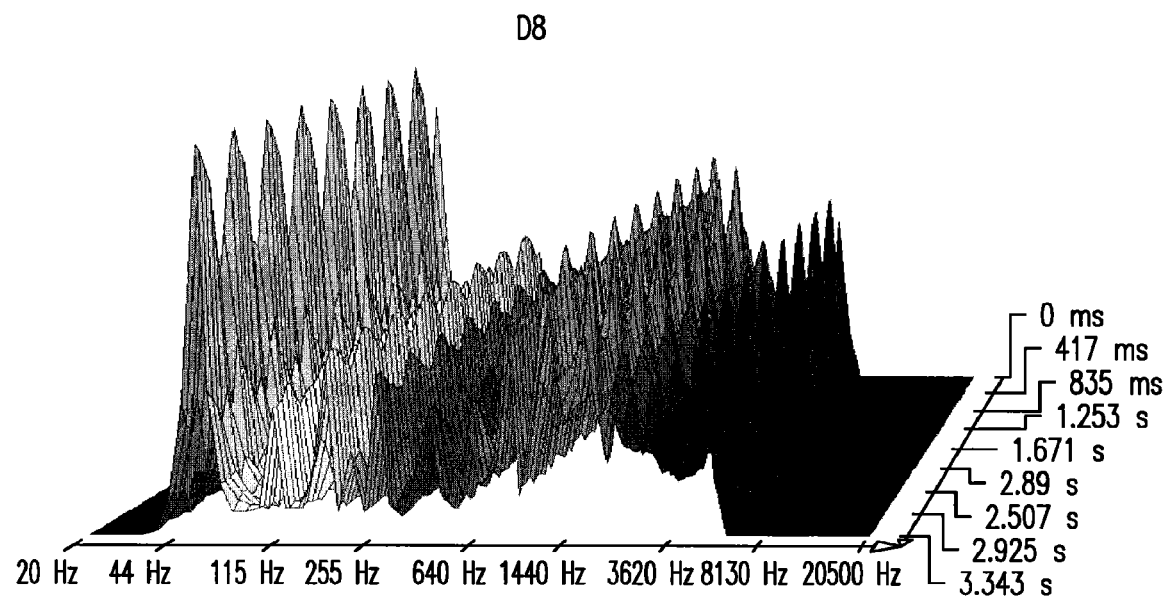
Figure 6I:
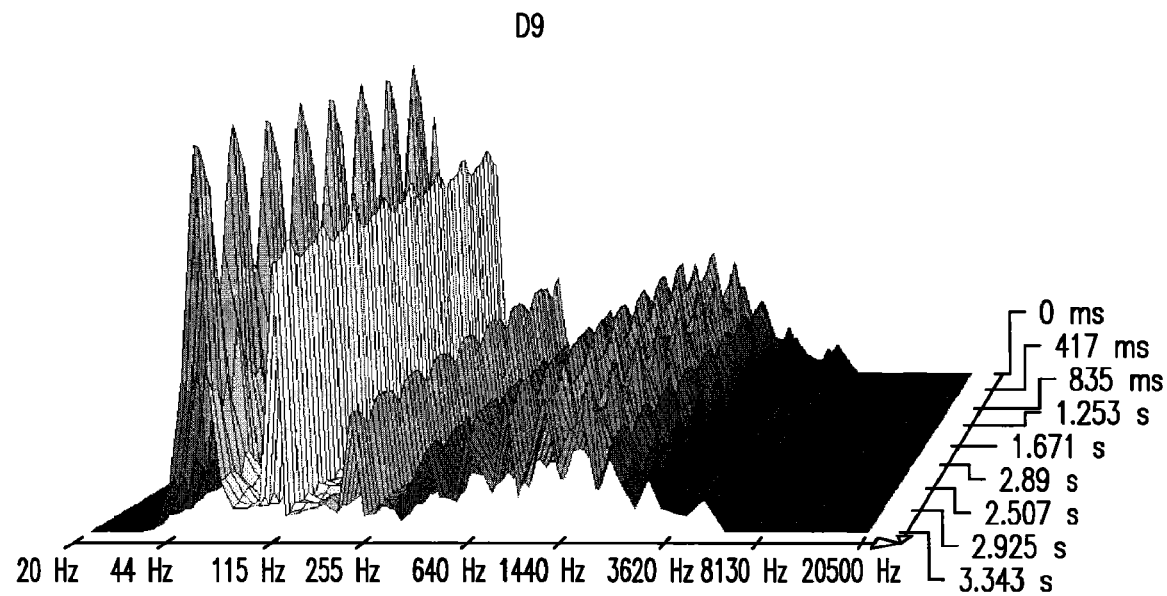
Figure 6J:
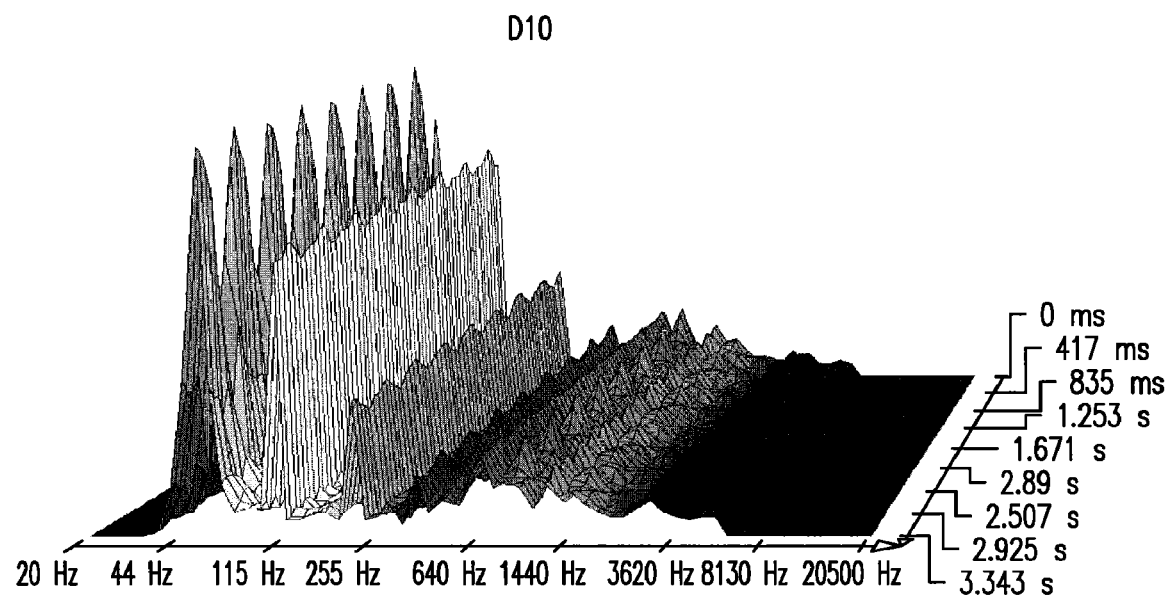
Figure 6K:
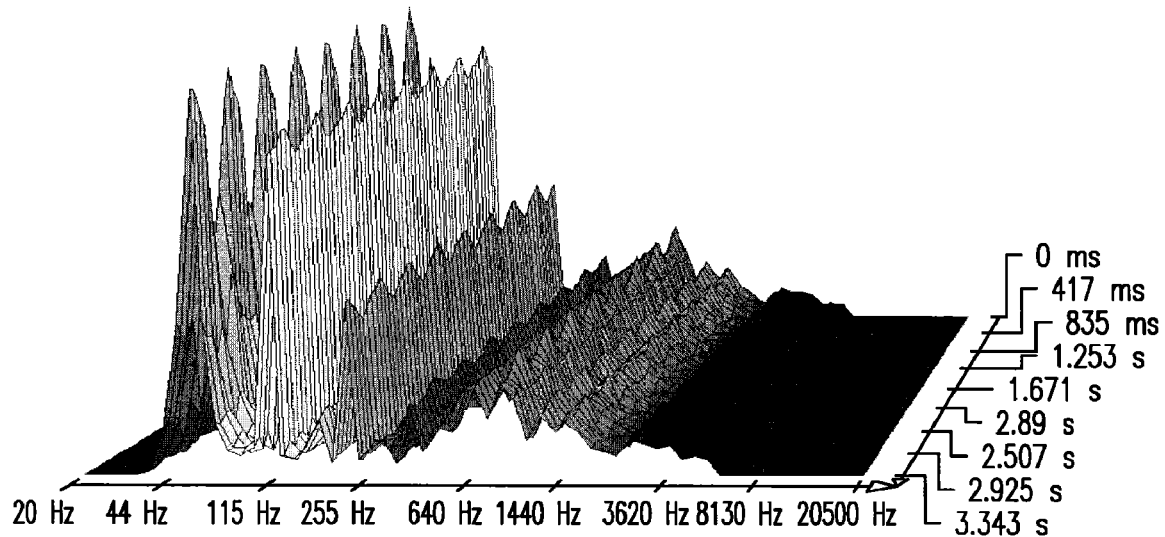
Figure 6L:
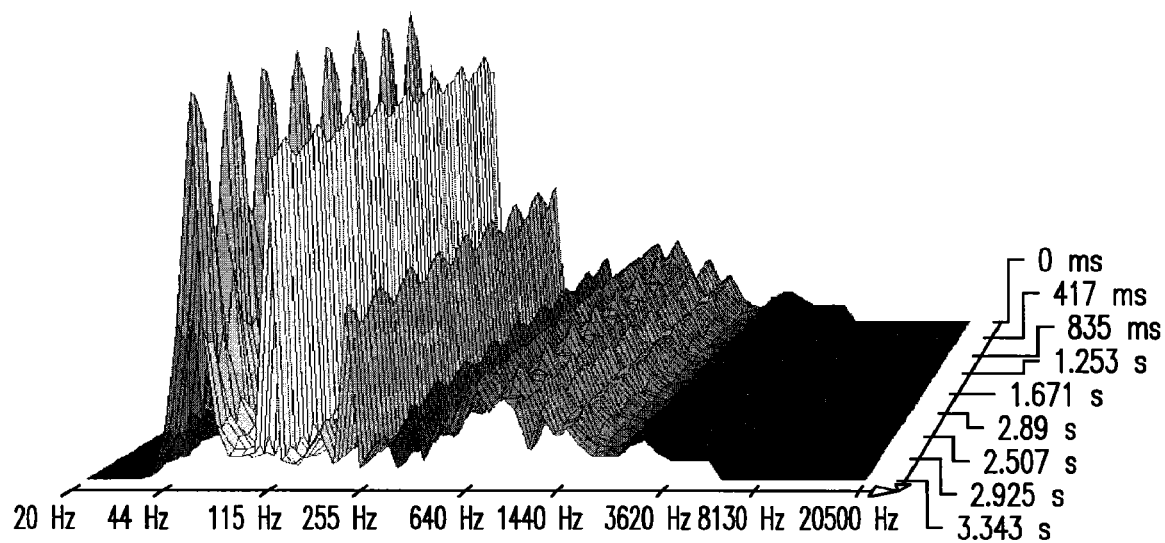

FIGS. 6A, B, C, D, E, F, G, H, I, J, K and L show the Fourier transformation analysis of the same samples as in FIGS. 5A, B, C, D, E, F, G, H, I, J, K and L. These graphs more easily show the EMS from the samples. Samples NF (FIG. 6A) to D4 (FIG. 6D) do not show any large peaks on the right side of the graph. However, beginning with sample D5 (FIG. 6E) and ending with sample D8 (FIG. 6H), the graphs show large peaks on the right side of the graphs indicating the emission of EMS from the EMS generating entity associated with HIV infection. Finally samples D9 to D12 reverted back to the pattern seen with background noise.

Figure 7A:
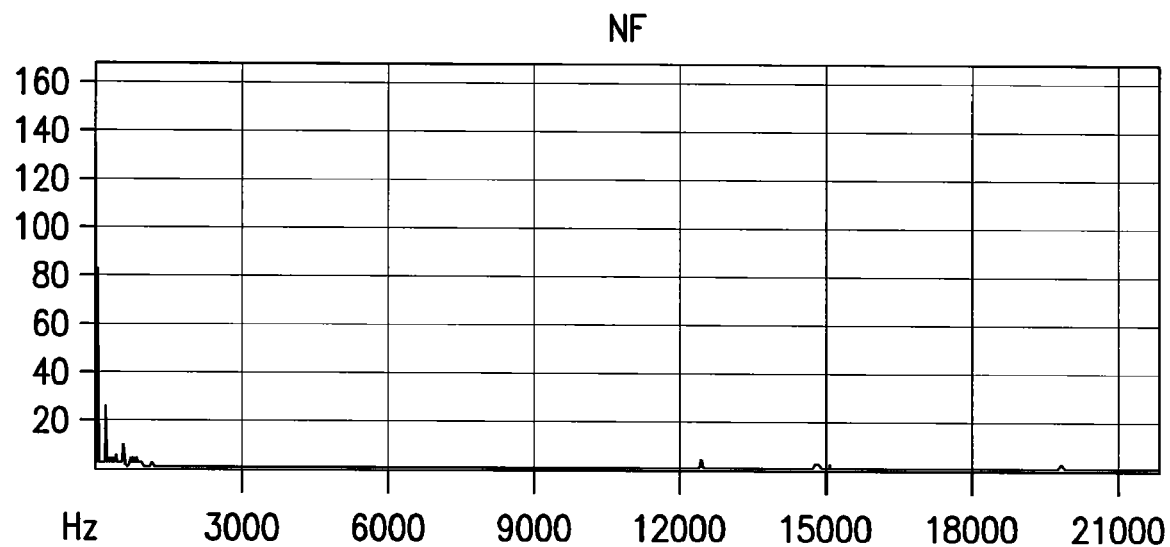
Figure 7B:
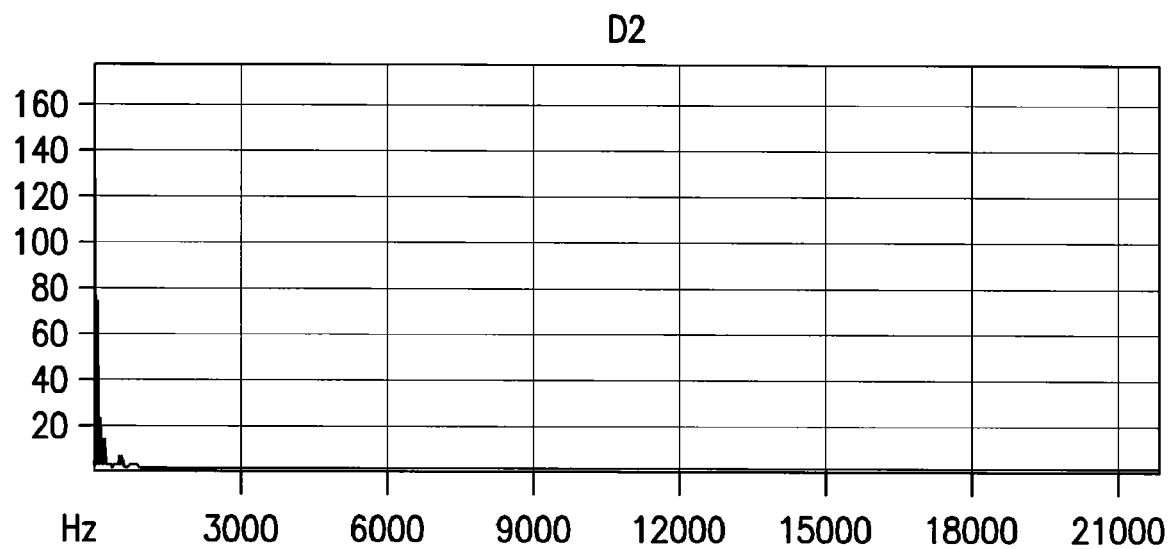
Figure 7C:
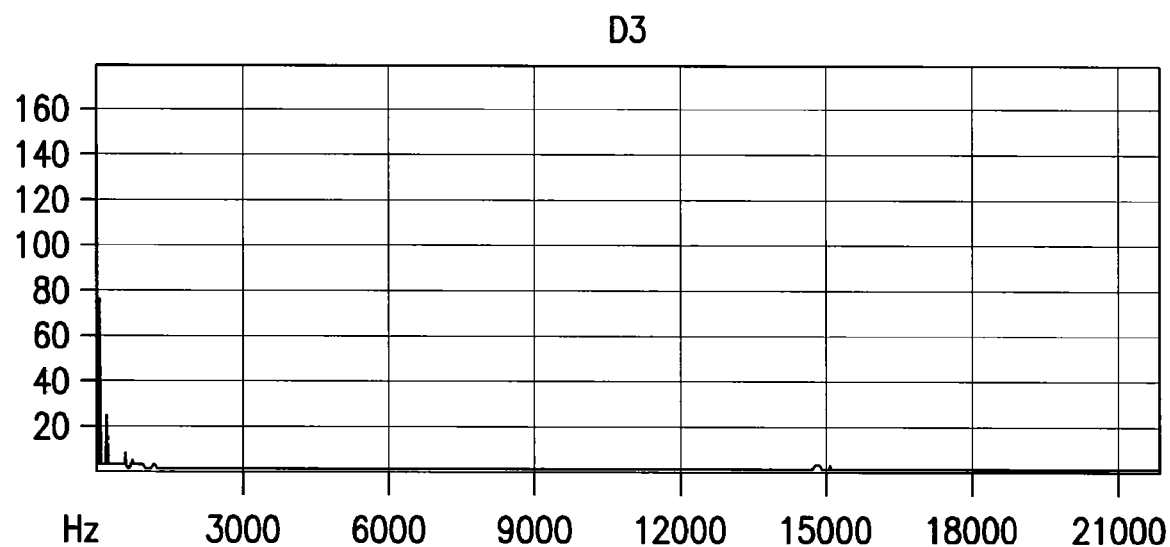
Figure 7D:
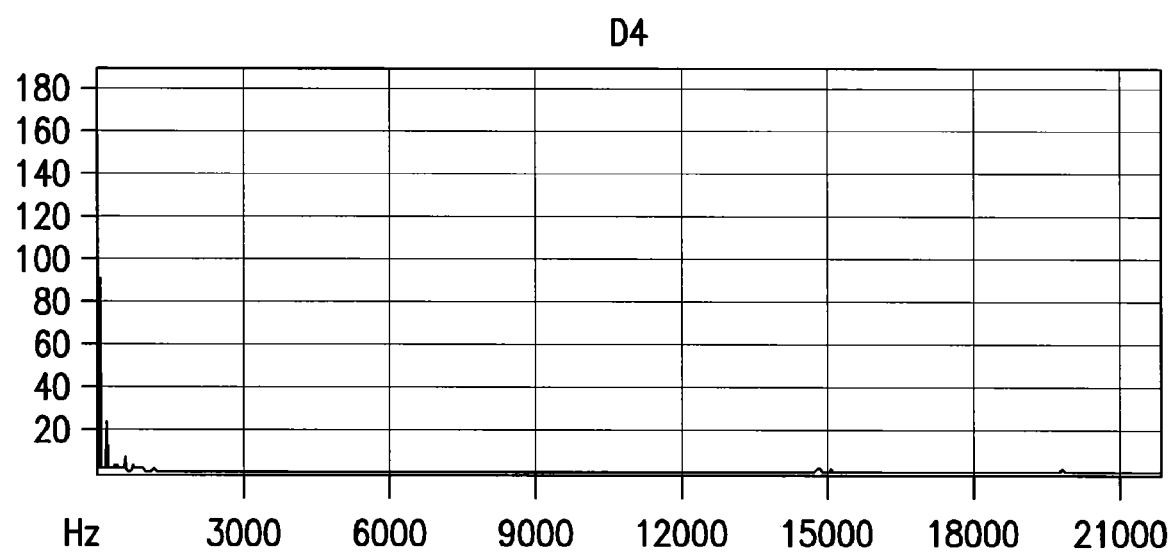
Figure 7E:
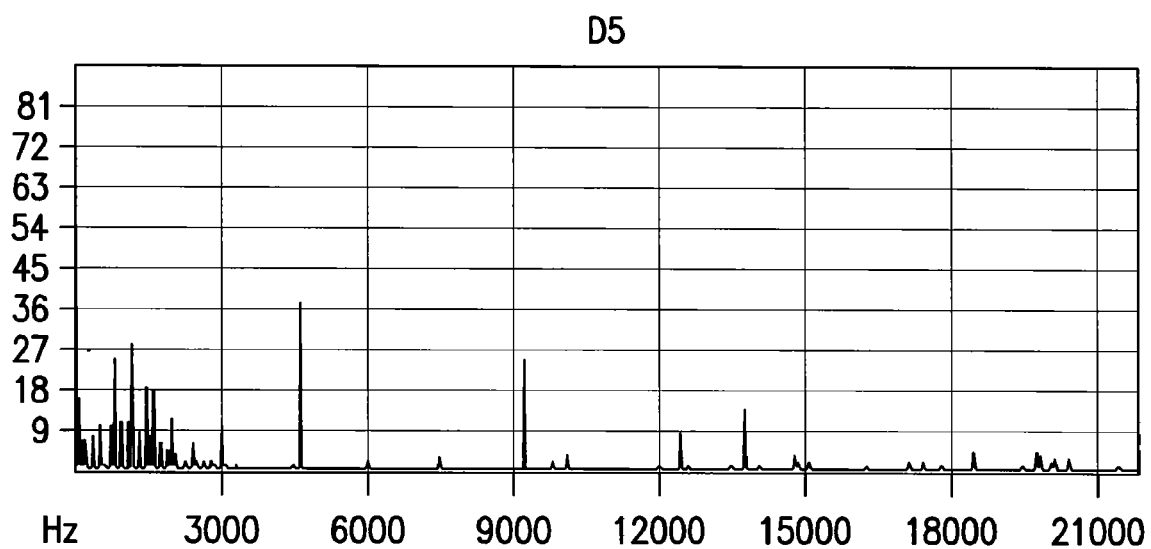
Figure 7F:
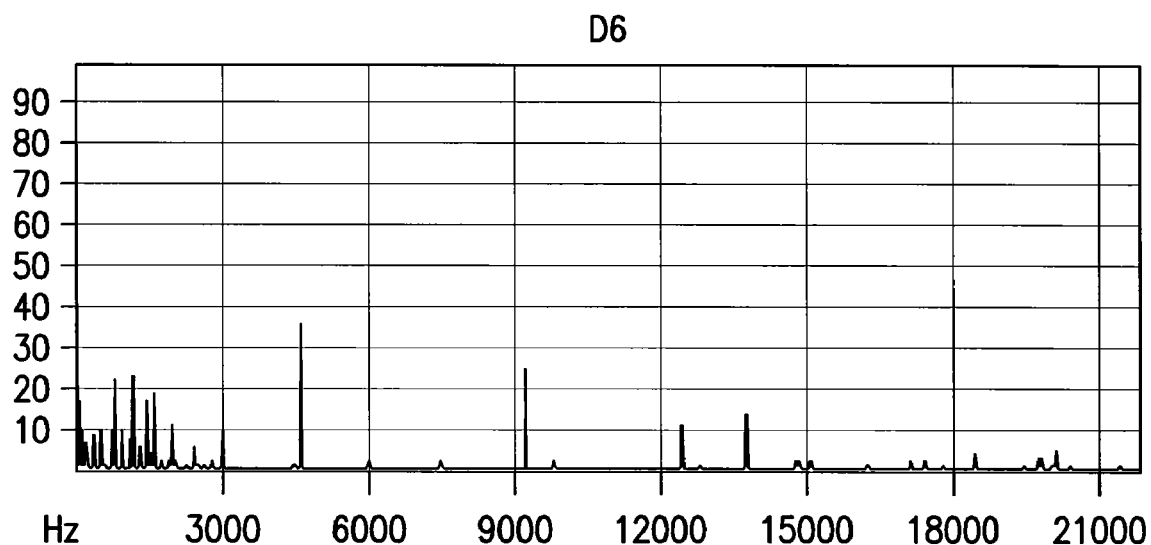
Figure 7G:
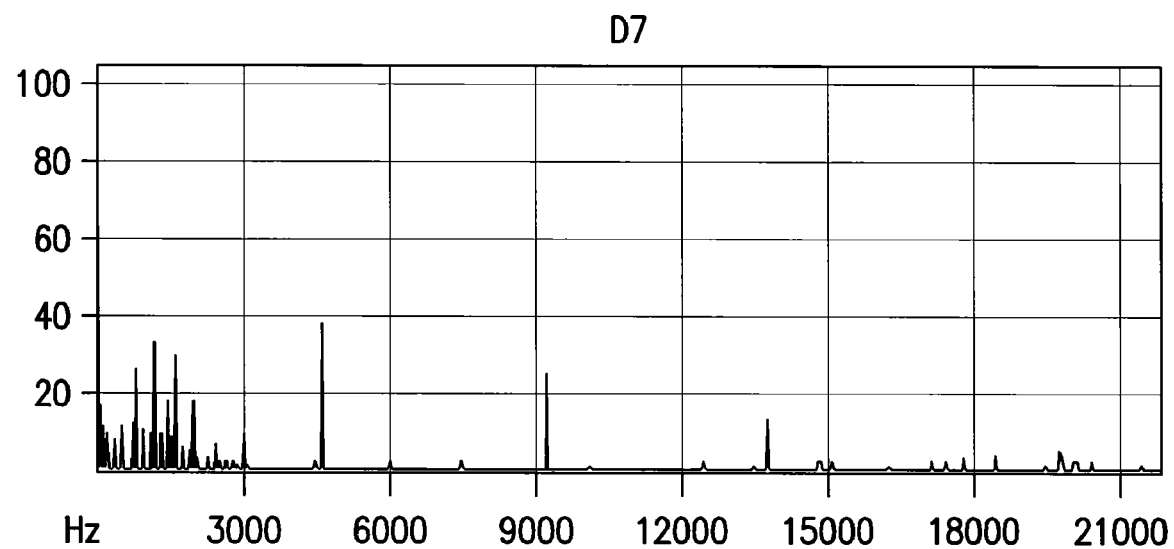
Figure 7H:
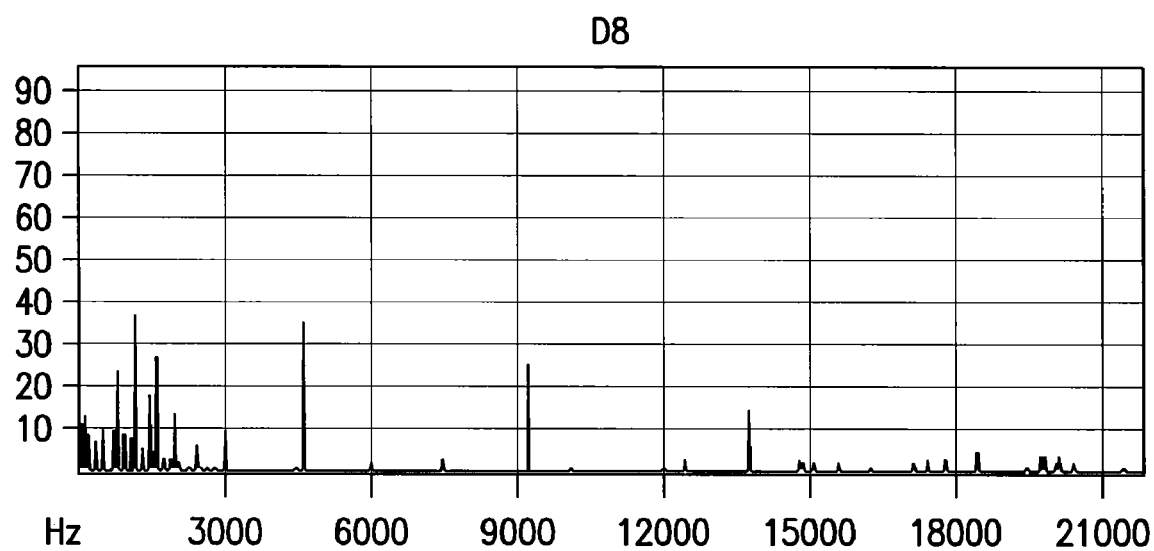
Figure 7I:
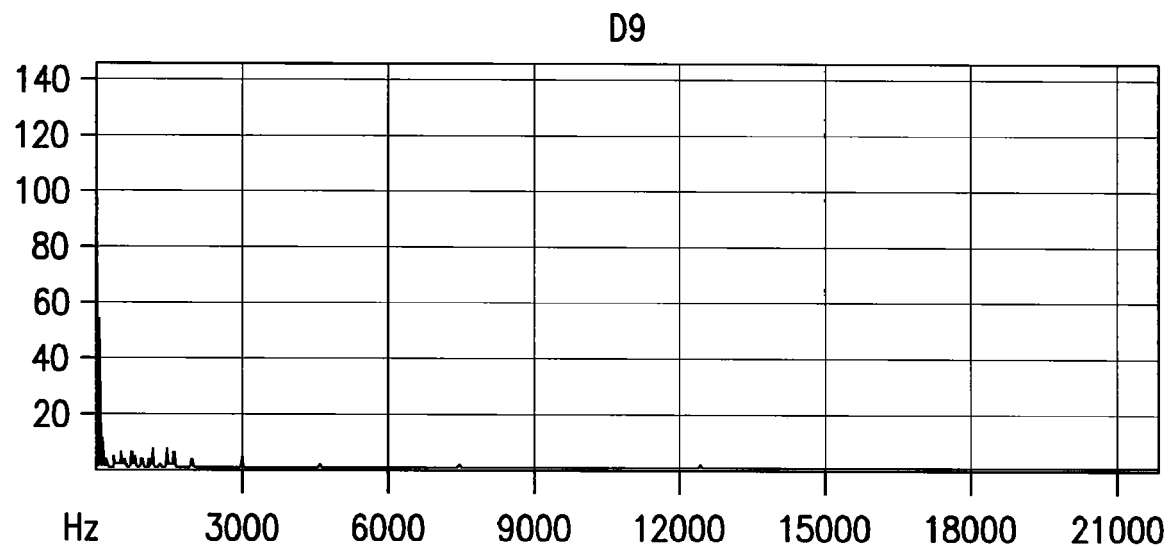
Figure 7J:
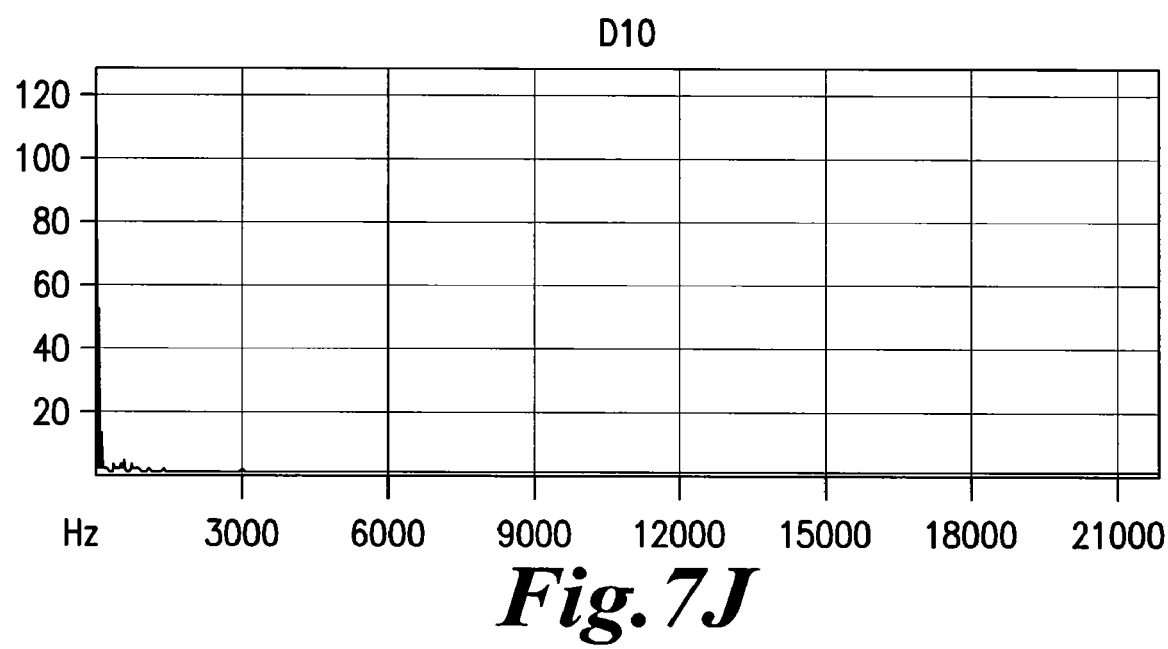
Figure 7K:
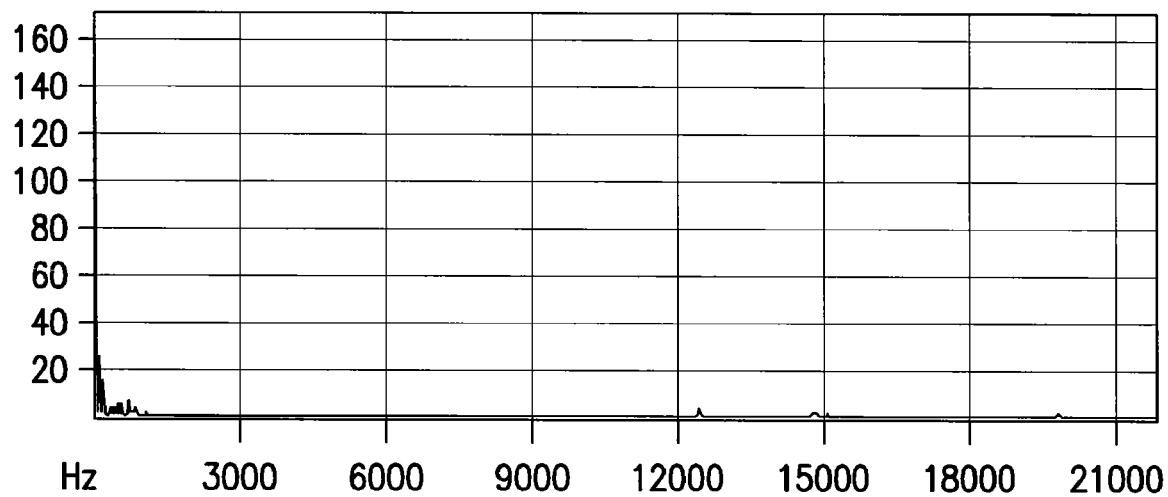
Figure 7L:
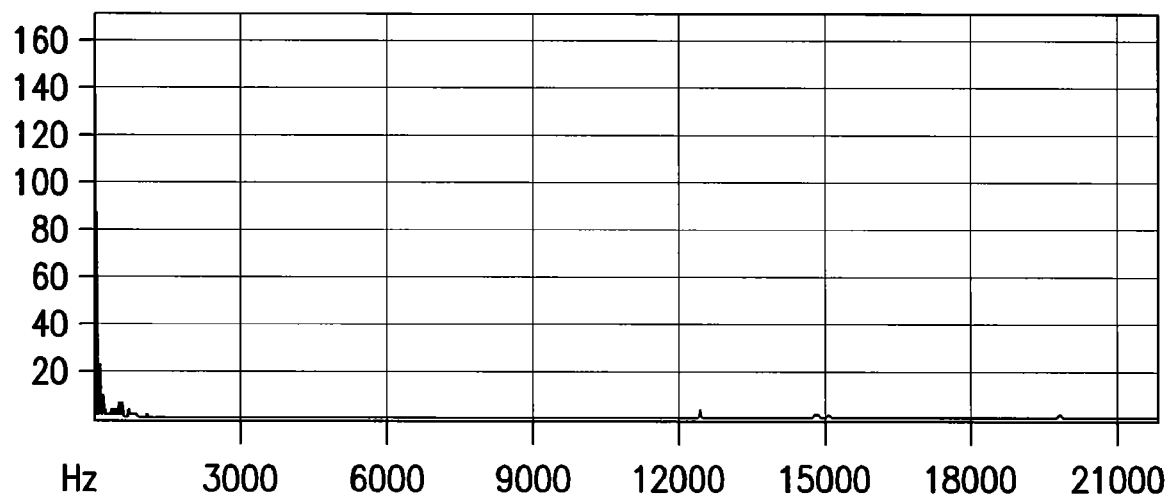

FIGS. 7A, B, C, D, E, F, G, H, I, J, K and L show the Fourier transformation analysis presented with spikes rather than waves as in FIG. 6. These graphs allow an easier analysis of the EMS from the samples. Samples NF (FIG. 7A) to D4 (FIG. 7D) and D9 to D12 (FIGS. I-L) do not show any spikes in the graph, which indicates the recording of just background noise. However, samples D5 to D8 (FIGS. 7E-7H) show many spikes near the origin and multiple spikes along the base of the graph. This pattern shows the EMS emission indicating the presence of nanostructures induced by HIV DNA.

EMS Recording Apparatus

Figure 8:
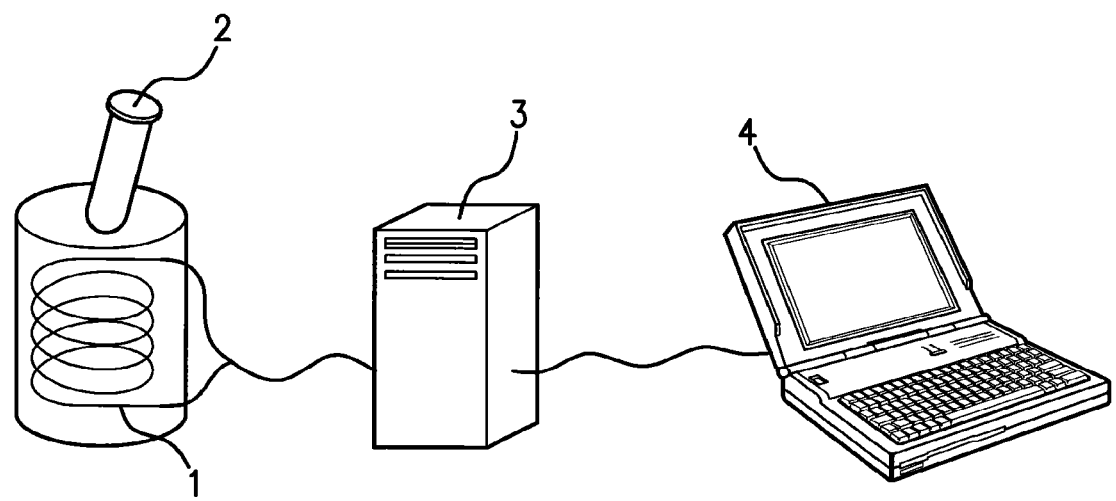

FIG. 8 shows a schematic representation of the equipment used to record EMS from samples. A coil, bobbin of copper wire, surrounded the sample vial (2) to detect the EMS. The wires from this coil were connected to a Sound Blaster Card (3), which in turn was connected to a laptop computer (4). A laptop computer is preferred since it can be run with battery power, which eliminates some background EMS from AC current. Each emission was recorded twice for 6 seconds, amplified 500 times and processed with different software for visualization of the signals on the computer's screen. The main harmonics of the complex signals were analyzed by utilizing several types of Fourier transformation software.

Increased Sensitivity of PCR

FIG. 9 is an electrophoretic gel showing the detection of DNA in each of the serial dilutions of a blood sample obtained from a patient positive for HIV and receiving ART. The sample was processed with two different methods: 1) the typical method of mixing the diluted sample between each serial dilution and 2) the improved method of vigorously vortexing the diluted sample between each serial dilution. The diluted samples were run on the gel to detect the DNA present in each dilution. The samples run on the gel were from NF (original undiluted sample) to D10 ($10^{-10}$). The NF band was the only band visible in the samples that were just mixed between each step of serial dilutions (upper). However, bands were visible for the NF, D2 ($10^{-2}$) and D3 ($10^{-3}$) samples when the samples were vigorously vortexed between each serial dilution (lower). This improved method showed an increase of sensitivity by 100 times over the typical methods used with PCR.

FIGS. 10A, B and C together depict Table A that shows the representative results of an experiment testing for EMS in patients with varying levels of HIV infection and antiretroviral therapy. The presence of EMS was tested in various samples from these patients: unfrozen blood plasma and samples with DNA extracted from a frozen blood sample—Plasma DNA, WBC (white blood cells) DNA and RBC (red blood cells) DNA. The first group of patients (B1-B4) was asymptomatic for HIV and had not received antiretroviral therapy. All samples from these patients, whether the sample was fresh plasma or DNA extracted from frozen blood, did not emit EMS at any dilution. These patients had HIV virus present in their samples, but their presence did not cause the emission of EMS. The second group of patients (C1-C4) (FIG. 10A) was asymptomatic for HIV and had received antiretroviral therapy. These patients' plasma and RBC DNA samples emitted EMS; however the WBC samples did not emit EMS and were silent. Also, it did not depend if the sample was from fresh plasma or DNA extracted from a frozen sample. Additionally, the dilution range for emitting EMS was very similar from sample source (Plasma, Plasma DNA, WBC DNA, and RBC DNA) and between patients (C1-C4) (FIGS. 10B and 10C). The dilution emitting EMS ranged from D3 ($10^{-3}$) to D9 ($10^{-9}$). It is important to note that the WBC DNA did not emit EMS, indicating that the EMS generating entity (probably DNA) was not present in these cells, although some of the WBC [CD4 lymphocytes and monocytes] are the target for the HIV virus. Additionally, the RBC DNA sample was positive for emitting EMS, even though RBC lack a nucleus. It is theorized that the EMS generating entity may be adsorbed to the exterior cell membrane of the RBC or associated with a cell that co-migrates with RBC during fractionation. Also, the EMS generating entity may have the same density as RBC and so be found in the RBC fraction. The third group of patients (D1-D4) (FIG. 10C) was symptomatic for HIV and had not received antiretroviral therapy, that is, showing full-blown AIDS. It is difficult to find patients in the Developed World in this condition due to the wide-spread use of antiretroviral therapy. However, it is very common to find patients with untreated AIDS in the Undeveloped World due to high cost of the antiretroviral therapy drugs and lack of money by the patients or their countries. During a trip to Central Africa, samples were obtained from patients with Full-Blown AIDS. Blood samples from these symptomatic untreated patients were found not to emit EMS. None of the samples, whether fresh or from frozen samples, were found to emit EMS. This finding suggests that the EMS generating entity is only produced when the virus replication has been inhibited by antiretroviral therapy. If the production of this EMS generating entity was just a step in the progression of the HIV infection, it would be expected in patients with a long duration of infection, that is in patients who are asymptomatic for AIDS and had not received antiretroviral therapy and patients who are symptomatic for HIV and had not received antiretroviral therapy, since both groups represent people with long-term HIV infections. The finding that samples from symptomatic untreated patients lacked EMS indicated that the process that produces the EMS generating entity was probably associated with some "self-preservation" mechanism of the HIV virus to hide from the immune system of the infected animal.

FIGS. 11A and B show representative results of an experiment testing for EMS from DNA bands resulting from PCR and nested-PCR. Five HIV genes (Gag, Pol, Env, LTR, & Nef) were amplified, isolated and samples prepared and diluted with serial dilutions. There were differences in the ability to emit EMS found between individual genes and whether the DNA was produced by PCR or nested-PCR. The Gag and Pol genes did not emit EMS from DNA produced by either PCR or nested-PCR (FIG. 11A). The Env, LTR and Nef genes showed EMS emission when the DNA was obtained using nested-PCR and the sample was diluted from $10^{-4}$ to $10^{-8}$ (FIG. 11B). These results indicated that the EMS may be associated with a specific gene or genes in the HIV virus. However, there may be other genes or nucleic acid sequences that emit EMS.

DETAILED DESCRIPTION OF THE INVENTION

The invention relates to the detection in a blood sample of electromagnetic signals coming from HIV DNA, in patients which have undetectable viral RNA in their blood as measured by commercial existing tests.

This new test will allow elaborating new therapeutics aimed at reducing the amount of this DNA, thus creating the possibility to eradicate the viral infection. In clinical sites, unfrozen plasma from fresh blood samples can be used and directly tested. Otherwise the plasma sample will have to be shipped in a frozen state and DNA can be extracted from this plasma, as well as, from blood cells, including those associated with the erythrocyte fraction, and also from any tissue or body fluid.

The technology of detecting EMS from pathogenic particles was refined and improved to the capture electromagnetic signals of HIV DNA sequences. Unlike the nanostructures induced in water by bacterial DNA, which passed through 100 nM filters but were retained by 20 nM filters, the HIV DNA nanostructures are smaller since they passed through 20 nM filters. The range of dilutions are lower at which the EMS from viruses could be detected, starting from $10^{-3}$ up to $10^{-9}$ decimal (i.e., 1 part sample:9 parts diluent] dilutions. There is no detectable difference in the profile of the signals at this level of technology, indicating that it is probably due to a resonance phenomenon of water polymers.

The material structures at the origin of the signals are unlikely to come from mature HIV virions, as they differ in density in sucrose gradient from the density of 1.16 of retroviruses. Moreover, in the blood of AIDS patients, they are produced by DNA and not RNA.

An important observation, although paradoxical, is that only HIV-related DNA sequences from patients treated with antiretroviral therapy and having no detectable RNA in their blood can be detected by EMS emission and by PCR. Naive untreated patients, either with high or low virus load, show no evidence of such DNA. This result was obtained with patients of different geographic locations (North America, Europe, West and Central Africa) presumably infected with different HIV subtypes.

Interestingly, this DNA is not only detected in the plasma fraction, but also found associated with the erythrocyte fraction. As there is no DNA in mature erythrocytes, the viral DNA is probably present in nanostructures bound to the erythrocyte membrane (exosomes) or in nucleated cells that sedimented with the erythrocytes (i.e., granulocytes). In treated patients still having a detectable virus load, the DNA was only found in the plasma fraction.

There are several possible source(s) of this DNA and possible roles by this DNA. PCR analysis of the prototype HIV 1 Lai DNA indicated that short fragments of nested-PCR amplified DNA, in picogram amounts, are the source of EMS, derived in particular from the LTR, Env and Nef genes. Similarly, in the case of patient DNA, the LTR, Nef and Env-derived amplicons were also EMS positive.

There may be in vivo DNA fragments corresponding to other genes which are not picked-up by the primers currently used. Therefore it is possible that the whole genome is represented as DNA fragments in the blood or even as an entire genomic molecule. The most simplistic explanation for the presence of this DNA is that it reflects the breakdown (e.g., apoptosis) of some infected cells containing the proviral DNA in a latent state. This would imply that after antiretroviral treatment, these cells die and constitute a reservoir large enough to be continuously refilled by new living cells. A priori, there is no reason that such cells, unless they express some HIV proteins recognized by cytotoxic T cells, will be destroyed by the immune reactions.

Possibly the DNA detected represents forms of unintegrated HIV DNA. Various circular DNA forms have been described during HIV infection in vitro and in vivo. Sharkey et al. have even described the persistence of episomal forms of HIV DNA in some patients treated by antiretroviral therapy with undetectable viral RNA in their blood. However their study was focalized in peripheral blood mononuclear cells (PBMC). However, our study could not detect HIV DNA in PBMC, indicating it comes from other cell types and tissues. Another possible theory is that the antiretroviral therapy works efficiently to prevent reverse transcription of viral RNA into DNA and therefore blocks any productive infection of susceptible cells. However it will not prevent DNA-DNA replication in a non-integrated state. In other words, the ART treatment pushed the virus towards an alternate way of replication, probably minor and depending on a cellular DNA polymerase, but sufficient to maintain the viral genetic information as unintegrated viral DNA and able to resume the normal viral cycle if ART is interrupted for any reason.

The DNA found in the blood circulation would then be a by-product of this DNA. The cells and tissues in which this DNA replication occurs have not been identified. This theory, if correct, would have some important implications for the eradication of HIV infection. If specific inhibitors can target this episomal replication, without damaging the cellular processes, a complete elimination of the HIV reservoir might be achieved and therefore eradication of HIV infection.

Experiments have indicated that this detection also applies at the scale of the human body: the same EMS has been detected in the plasma and in the DNA extracted from the plasma of patients suffering of Alzheimer, Parkinson disease, multiple Sclerosis and Rheumatoid Arthritis.

The physical nature of the nanostructures which support the EMS resonance remains to be determined. It is known from the very early X-ray diffraction studies of DNA that water molecules are tightly associated with the double helix, and any beginner in molecular biology knows that DNA in water solution forms gels associating a larger number of water molecules. Moreover, a number of physical studies have reported that water molecules can form long polymers of dipoles associated by hydrogen bonds (Ruan et al., 2004; Wernet et al., 2004). However these associations appear to be very short-lived (Cowan et al., 2005).

EXAMPLES

Example 1

Measurement of Electromagnetic Signals

The plasma or DNA solution [1-4 ng/ml] is dissolved in Phosphate Buffered Saline (PBS) at the concentration of $10^{-2}$, then filtered on Millipore 0.45 micrometer filter and the filtrate is refiltered on Anotop Whatman filter of 20 nanometer porosity. The filtrate is then diluted in distilled water in 1.5 ml Eppendorf conical plastic tubes in serial 1 part sample:9 parts diluent [decimal] dilutions ranging from $10^{-2}$ to $10^{-15}$ and strongly agitated on a vortex for at least 15 seconds.

Plasma is prepared by centrifugation of heparinized blood of patients presenting with conditions of: 1) Asymptomatic, untreated; 2) Symptomatic, not yet treated, with high virus load; or 3) Symptomatic, treated by antiretroviral therapy with no detectable virus load by commercial kits (<200 RNA copies/ml).

EMS was only detected in the plasma of the third category (30 out of 30), in plasma dilutions ranging from $10^{-5}$ to $10^{-8}$. Results with the two first categories were generally negative, with the exception of one untreated AIDS patient.

The conditions of preparation and storage of the plasma sample was determined for optimizing the capture of EMS. The plasma had to be kept unfrozen, preferentially stored at +4° C. Freezing and storing at −20° C. or −80° C. destroyed their capacity to produce EMS, unless DNA was extracted, the primary source of the signals.

Serum taken from the clotted blood was also negative, whether kept at +4° C. or frozen. Heating the diluted $10^{-2}$ plasma at 65° C. for one hour also inactivated or reduced significantly the EMS.

Example 2

The Decay with Time of EMS Production in Plasma Stored at +4° C.

The capacity to emit EMS in plasma can last for several days, sometimes for several weeks of storage, indicating a relative stability of the nanostructures that emit EMS in the plasma proteinic environment. In vitro studies indicated that filtration of the plasma (usually at the 1/100 dilution in PBS or saline) through 20 nM filters was a prerequisite for detecting the signals in further dilutions of water. In some rare cases, weaker signals can be detected at lower dilutions after filtration through 100 nM porosity filters. Positive signals were usually found in the range of the $10^{-3}$ to $10^{-9}$ dilutions.

Example 3

Evidence that Positive Signals Come from DNA

Experiments were conducted to determine if nucleic acids carrying the genetic information for HIV, either residual viral RNA or proviral DNA, could be the sources of signals in the plasma of infected patients. Three groups of patients: infected and not treated in the asymptomatic stage; infected and not treated in the symptomatic stages; and infected and treated with ART with no detectable viral load.

Plasma was diluted 1/100 in PBS and the nucleic acids were extracted by the phenol-chloroform method. The solution was precipitated with ethanol and the precipitates were solubilized in water. The solution was filtered through a 20 nM filter at a concentration ranging from 1 ng/ml to 4 ng/ml.

EMS emissions were detected only in the group of patients treated by antiretroviral therapy and having an undetectable virus load. The signals were produced in the same range of aqueous dilutions than fresh plasma. Filtration of the original solution (1/100 dilution) and vortex agitation of each of the further aqueous dilutions was necessary in order to capture the EMS emission.

TABLE 1

DNA Solution, filtered 450 nM, then 20 nM, 2 ng/ml

|  | Control untreated 10 mM Tris-HCl, pH 7.4 | +RNase (10 μg/ml) 10 mM Tris-HCl, pH 7.4 37° C./2 hours | +DNase (10 U/μg) 10 mM Tris-HCl, pH 7.4, MgCl$_2$ 37° C./2 hours |
|---|---|---|---|
|  | ↘ | ↓ | ↙ |
|  |  | Freezing −20° C./2 hours |  |
|  | ↙ | ↓ | ↘ |
| EMS Range of dilutions | positive D5-D9 | positive D5-D9 | negative |

Treatment by RNase (10 g/ml, 1 hour at 37° C.) of the original solution had no effect. This suggested that DNA, rather than viral RNA, was involved in EMS production. Confirmation was obtained by DNase inactivation. However this only occurred if the sample, which previously had EMS, was frozen and thawed before the DNase treatment. If the sample was not frozen, then the sample would continue to have EMS after DNase treatment. It is believed that nanostructures previously induced by the DNA in the water remain after DNase treatment, if they have not been eliminated by freezing or other treatments that are known to eliminate EMS emitting from samples. However DNA molecules are not affected by freezing and the DNA can re-induce the water nanostructures after the specimen is thawed. The experimental protocol and results are shown in the following table.

Plasma, plasma DNA and erythrocyte DNA were obtained from patients or individuals in different conditions: 1) naive (untreated) positive patients at the asymptomatic stage; 2) naive patients with full blown AIDS and high virus load; 3) AIDS patients treated by antiretroviral therapy (usually 2 nucleosidic reverse transcriptase inhibitors and 1 non-nucleosidic reverse transcriptase inhibitor or 1 protease inhibitor) and having undetectable virus load (viral RNA copy number inferior to 40/ml of blood) and 4) uninfected controls. At least 10 patients of each group were tested.

The third group was the only one that showed positive electromagnetic signals, both in fresh plasma or in DNA extracted from frozen plasma. The DNA extracted from the erythrocyte pellet (probably containing some nucleated cells such as granulocytes) was also positive.

If the treated patient still had a high viral load upon treatment, only the plasma DNA was positive. This was also the case of pregnant women treated by viral inhibitors in the last trimester of their pregnancy.

No untreated patient was positive in any of the three fractions: plasma DNA, red cell pellet DNA, and leukocyte layer DNA.

The DNA was identified as representative of HIV DNA by the following:

using an infectious HIV DNA clone, derived from a prototype laboratory strain, and (HIV 1 Lai) containing all HIV genes, electromagnetic signals were detected from water solution in the same range of dilutions.

Specific Polymerase Chain Reaction (PCR) primers were used for the different gene sequences of HIV DNA (LTR, Pol, Env, Nef) these sequences were amplified from the DNA of patients positive for the electromagnetic signals. After a second round of amplification (nested PCR), these solutions induced the signals at similar dilutions as the whole DNA.

It also was noted that some specific sequences (LTR and to a lower extent Nef) were detected by RT-PCR (using reverse transcriptase as first polymerase), which resulted in a higher sensitivity.

Additionally, the obtained DNA bands were of higher intensity and increased sensitivity (10x-100x.) when the DNA dilution to be used for amplification was thoroughly vortexed in the same manner as used for preparations used to detect the electro-magnetic signals (EMS).

RNase treatment of the DNA before RT-PCR (10 g/ml, 2 hours, 37° C.) did not affect the results. This observation indicated that the reverse transcriptase was not using RNA, but a DNA template or another template as yet unidentified.

The detection of HIV DNA only in patients treated with antiretroviral therapy and having undetectable viral RNA in their blood indicated that the antiretroviral therapy had modified the mode of virus replication. It is believed that renewed virus replication, after the cessation of an antiretroviral therapy, begins from integrated or unintegrated proviral DNA.

Therefore, this DNA is an important biomarker of the HIV reservoir which persists after antiretroviral therapy, which opens the way for new types of treatment aimed at eradicating the infection.

Example 4

Location of the Active DNA in Blood Fractions

The heparinized blood of several HIV+ ART-treated patients was run on a Ficoll gradient. DNA was extracted from the three main fractions: plasma (with platelets), white cells layer and the erythrocyte pellet. Each DNA extract was tested for EMS emission.

In all the patients with undetectable virus load, only the DNA from the plasma and the erythrocyte fractions gave strongly positive signals. The white cell layer-derived DNA gave no signal or weak signals. In ART-treated patients with remaining high virus load, only the plasma-derived DNA was positive.

Fractionation on Ficoll Gradient

Peripheral whole blood from patients was collected in vacutainer tubes containing lithium heparin. 3 ml of whole blood were diluted with 10 ml phosphate buffered saline (PBS) buffer and layered over 3 ml of Ficoll-paque (1.077 g/ml density; Amersham Biosciences) in 15 ml Leucosep® tubes and centrifuged at 1000.times.g for 10 min at 4° C. Plasma was removed; the red blood cell (RBC) pellet and the white blood cells (WBC) were washed 2 times with 10 ml of PBS and centrifuged at 250×g.

DNA Extraction

Plasma DNA, WBC DNA and RBC DNA were extracted by Proteinase K in the presence of SDS (sodium dodecyl sulfate) and further deproteinized by phenol-chloroform mixture. The pellet obtained by ethanol precipitation was resuspended in Tris $10^{-2}$ M, pH 7.6 and an aliquot was diluted 1/100 in water. The dilution ($10^{-2}$) was filtered first through a 450 nM filter and the resulting filtrate was then filtered again on a 20 nM filter Anotop (Whatman). The filtrate was further diluted in serial decimal (i.e., 1:9) dilutions in water.

Detection of EMS

The filtrates from plasma were analyzed just after filtration for production of electromagnetic waves of low frequency. A device was used that been previously designed by Benveniste and Coll (1996; 2003) (incorporated by reference) for the detection of signals produced by isolated molecules endowed with biological activity. Briefly, 100 nM or 20 nM filtrates are serially diluted 1 in 10 (0.1+0.9 in sterile water (medical grade). The first 2 dilutions (1/10 and 1/100) were done in serum-free RPMI medium, in order to avoid eventual protein precipitation in deionized water. Each dilution was done in 1.5 mL Eppendorf plastic tubes, which are then tightly stoppered and strongly agitated on a Vortex apparatus for at least 2 seconds, up to 15 seconds or more. This step has been found important for the generation of signals. After all dilutions have been made (generally 15-20, 1:10 dilutions), the stoppered tubes were read one by one.

EMS Measurement

To capture and analyze the EMS, a coil, bobbin of copper wire, was used and connected to a Sound Blaster Card itself connected to a laptop computer, preferentially powered by its 12 volt battery. Each emission was recorded twice for 6 seconds, amplified 500 times and processed with different software for visualization of the signals on the computer's screen. The main harmonics of the complex signals were analyzed by utilizing several types of Fourier transformation software.

In each experiment, the internal noise generated by the different pieces of the reading system was first recorded (coil alone, coil with a tube filled with water). Fourier analysis shows that the noise was predominantly composed of very low frequencies, probably generated at least in part by the 50/60 Hz ambient electric current. The use of the 12 V battery for the computer power supply did reduce, but not abolish this noise, which was found to be necessary for the induction of the resonance signals from the specific nanostructures. When dilutions of the HIV virus filtrate were recorded for wave emission, the first obvious phenomenon observed was an increase of the overall amplitude of the signals at certain dilutions over the background noise and also an increase in frequencies. This change was abolished if the tube to be analyzed was placed inside a box sheltered with sheets of copper and Mu-METAL® (Magnetic Shield Corp., Bensenville Ill.). Fourier analysis of the HIV virus signals showed a shift towards higher frequencies close to 1000 Hz and multiples of it. Profiles were identical for all the dilutions showing an increase in amplitude. The first low dilutions were usually negative, showing the background noise only. Positive signals were usually obtained at dilutions ranging from $10^{-5}$ to $10^{-8}$ or $10^{-12}$. Higher dilutions were again negative. The positive dilutions varied according to the type of filtration, the 20 nM filtrate being generally positive at dilutions higher than those of the 100 nM filtrate. The original unfiltered suspension was negative at all dilutions, a phenomenon observed for all preparations analyzed.

Nature of the HIV Sequences at the Origin of EMS

It was determined from previous experiments that a single gene or even a fragment of a gene was sufficient to produce the EMS. Therefore an infectious DNA clone of HIV was used to test for EMS. The infectious DNA clone of HIV had been previously constructed from HIV LAI to determine which part of the viral genome was at the origin of EMS. To this end, some specific primers were designed for sorting out the main sequences corresponding to the different structural and regulatory genes of HIV, including LTR, Pol, Gag, Env, Nef, and Vif.

The amplicons and secondary amplicons resulting from nested-PCR were analyzed by agarose gel electrophoresis and yielded the expected fragment sizes. The DNA bands were extracted and purified, and assayed for EMS production at different dilutions. As a control, the entire HIV DNA genome isolated from a plasma was also tested and found positive for EMS. Several sequences (LTR, Nef and Env) were found to be a source of EMS.

The same primers were used to detect specific sequences in the DNA extracted from the plasma or the red blood cell pellet of the positive patients. The amplified LTR DNA fragment, visualized as a band of 104 bp by nested PCR, was constantly found in all preparations, followed infrequently by Nef and Env amplified fragments. Sequencing of the LTR band confirmed its HIV origin with 99% identity with the prototype HIV DNA (2 nucleotide differences out of 104). Interestingly, a higher sensitivity of detection was obtained by the use of reverse transcriptase (RT) before the use of the Taq polymerase in the PCR reaction.

However this reaction was not affected by prior RNAse treatment, indicating that a DNA template, not RNA, was also used by the RT enzyme.

In addition when aqueous dilutions were tested, a 10 to 100 times increase (1 to 2 decimal dilutions) of sensitivity was obtained, when each dilution was strongly agitated by vortex, as done for the detection of EMS.

Example 5

Increased Sensitivity of PCR

A method was developed that increases the sensitivity of PCR by 10 to 100 times over the current PCR technique, A sample containing DNA is filtered, and then serially diluted by 1/10 [1 part sample to 9 parts diluent] at each step in the dilution cycle which includes vigorous vortexing of the current dilution before proceeding to the next dilution in the series.

Another aspect of the method, which can be combined with the vigorous vortexing of the sample, is to treat the sample with an RNase. The sample is first filtered and then treated with an RNase. After the RNase treatment, the sample is processed as described above with serial dilutions (1 part sample to 9 parts diluent) with vigorous vortexing between each serial dilution.

Vigorous vortexing is defined as more than mere the quick vortexing done with samples in a laboratory. The vortexing should be sustained for several seconds to ten's of seconds. Samples in the experiments were routinely vortexed for 15 seconds or more, and this vortexing was repeated after each dilution. The vigorous vortexing of the diluted sample is important in obtaining the increased sensitivity. The vigorous vortexing of the sample is believed to cause the DNA to induce nanostructures. The samples can be analyzed with PCR, nested-PCR, RT-PCR, or nested-RT-PCR.

PCR Primers

PCR primer sequences were retrieved from the online Primer Bank data base, These primers were synthesized at the Molecular Biology Core Facility, Massachusetts General Hospital. Both UV absorbance and capillary electrophoresis were used to assess the quality of primer synthesis.

One-step reverse transcriptase (RT)-PCR experiments were performed with the Mastercycler® ep (Eppendorf). A 50 µl RT reaction included 25 µl of 2×RT-PCR buffer, 16.6 µl of nuclease-free-water, 0.4 µl of 25 mM of each deoxynucleoside triphosphate (dNTPs), 1 µl of 50 µM of each appropriate primer (Invitrogen), 1-4 ng/ml of total DNA and 1 µl of iScript RT (BioRad). The RT-PCR mixtures were pre-heated at 42'C. for 30 minutes (RT step) followed by 1 cycle (inactivation and denaturation step) at 95° C. for 3 minutes, followed by 42 PCR cycles of amplification (95° C.

for 30 seconds; 56° C. for 30 seconds; 78° C. for 2 minutes). A final extension step was performed at 78° C. for 10 minutes.

The PCR mixture (50 µl) contained 29.4 µl of nuclease-water-free, 5 µl of 10.times. Taq PCR buffer, 8 µl of 25 mM MgCl$_2$, 0.4 µl of 25 mM dNTPs, 1 µl of 50 µM of each appropriate primer, 5 µl of RT-PCR product and 1 µl of 5 U/µl Taq DNA polymerase (Invitrogen).

The PCR was performed with the Mastercycler® ep (Eppendorf). The PCR mixtures were pre-heated at 95° C. for 3 minutes (inactivation and denaturation step), followed by 42 PCR cycles of amplification (95° C. for 30 seconds; 56° C. for 30 seconds; 78' C. for 2 minutes). A final extension step was performed at 78° C. for 10 minutes.

Specific internal primers were used for the second round of amplification [nested-PCR].

The amplification products were separated on a 1.2% Agarose gel electrophoresis/EtBr gel and visualized using a Molecular Imager® Gel Doc™ XR System (BioRad).

Infected CEM Cells

In vitro experiments were set up in which CEM cells were infected with a prototype HIV-1 strain, HIV LAI. Prior to the experiments, cells and infecting virus were first checked for *mycoplasma* contamination by using a highly sensitive PCR technology based on 16 s ribosomal RNA. Traces of *Mycoplasma arginini* were found only in control CEM cells, but no electromagnetic signals (EMS) could be detected in the culture supernatant of such cells.

By contrast, EMS was detected in dilutions of the culture supernatant of the HIV-infected cells, when the cytopathic effect was obvious. Filtration through 20 nM filters was found to be necessary to detect the EMS, indicating that the source of the EMS was smaller than this size and therefore smaller than the intact virus particles whose diameter range between 100 to 120 nM.

The density of such particles was evaluated by centrifuging to equilibrium an aliquot of the infected CEM supernatant on a sucrose density gradient with conditions where HIV virions form a sharp band at the density of 1.16.

By contrast, the nanoparticles producing the EMS were associated with fractions ranging in densities from 1.15 to 1.25. A longer time of centrifugation used to improve the density equilibrium did not modify this profile.

Analysis of Dilutions Versus EMS Emission

The lower dilutions, which logically should contain a larger number of signal-producing structures, were "silent". When 0.1 mL of a negative low dilution (e.g. $10^{-3}$) was added to 0.4 mL or 0.9 mL of a positive dilution ($10^{-8}$), the latter became negative. This indicated that the "silent" low dilutions were self-inhibitory, probably by interference of the multiple sources emitting in the same wave length or slightly out of phase, like a radio jamming. Alternatively, the abundance of nanostructures can form a gel in water and therefore are prevented to vibrate.

Influence of Order of Reading Samples to Emitting EMS

The results were independent of the order in which the samples were read, whether in descending dilutions from to the lowest to the highest or in ascending dilutions from the highest to the lowest. Diluted samples placed in a random order (labels unknown to the person reading the samples) indicated the same range of positive dilutions was detected, if each tube was well separated from the other, to avoid their "cross talk". The results were also independent of the location of the reading site. Even though the background noise was variable, according to the location and time of recording (generally higher in large cities than in isolated areas), positive signals were always clearly differentiated over the background by higher frequency peaks.

Nature of the Aqueous Nanostructures:

Treatments by RNAse A (Promega, 1 µg/ml, 37° C., 1 hour), DNase I (Invitrogen, 10 U/µg DNA, 37° C., 18 hours), Lysozyme (Fisher, 1 mg/mL, 37° C., 10 minutes), Proteinase K (Promega, 0.12 mg/mL, in 1% sodium dodecyl sulphate, 56° C., 1 hour) did not suppress the EMS producing activity of the "loud" dilutions nor did activate the "silent" dilutions. However, heating at 70° C. for 30 minutes suppressed irreversibly the activity, as well as did freezing for 1 hour at −20° C. or −60° C. DMSO (10%), and formamide (10%) had no effect. Treatment with lithium cations, known to affect the hydrogen bonding of water molecules, was able to reduce the intensity of the signals, while the range of the positive dilutions remained unchanged.

Nature of the Origin of the Nanostructures:

In preliminary experiments, it had been observed that a pretreatment of a suspension of bacteria did not alter its capacity to induce the electromagnetic signals, even though it killed the virus. This treatment degraded the viral RNA without attacking double-helical DNA. This suggested that the source of the signals may be the DNA itself. Likewise, DNA extracted from HIV infected samples by the classical phenol: chloroform technique was able upon filtration and appropriate dilutions in water to emit EMS similar to those produced by HIV virus under the same conditions. DNAse treatment of the extracted DNA solution abolishes its capacity to emit signals, at the condition that the nanostructures previously induced by the DNA are destroyed.

Sample Analysis

A sample was treated by Proteinase K in the presence of SDS (sodium dodecyl sulfate) and further deproteinized by phenol-chloroform mixture. The pellet obtained by ethanol precipitation was resuspended in Tris $10^{-2}$ M, pH 7.6 and an aliquot was diluted 1/100 in water. The dilution ($10^{-2}$) was filtered first through a 450 nM filter and the resulting filtrate was then filtered again on a 20 nM filter. The filtrate was further diluted in serial 1:10 dilutions in water as previously described. As for the intact microorganisms, the filtration step was found to be essential for detection of the EMS in the DNA dilutions. In its absence, no signals could be detected at any dilutions. In contrast to the HIV viral suspension, where the filtration was supposed to retain DNA, the filtration at 20 nM did not retain the DNA, which was still present in the filtrate, as measured by optical density. In the case of DNA, the role of the 20 nM filtration is probably to dissociate the network of nanostructures organized in a gel-like liquid crystal at high concentrations in water, allowing their dispersion in further dilutions. The dilutions positive for EMS were in the same range that those observed for the viral suspensions, generally between $10^{-7}$ to $10^{-13}$.

DNA Content of Dilutions

At the high dilution of $10^{-9}$, calculations indicated that there is no DNA molecule of MW larger than $10^5$ in the solution, making it unlikely that the EMS were produced directly by the DNA itself, but rather by the self-sustained nanostructures induced by the DNA. Further demonstration that the EMS produced came from DNA was shown by their disappearance after DNAse treatment. This inactivation was however only complete when the nanostructures induced in the DNA solution which were themselves resistant to DNAse were previously fully destroyed. This destruction was obtained either by freezing the DNA solution at −20° C. for 1 hour or heating it at 90° C. for 30 minutes. After slow cooling to allow the heated DNA to reanneal, DNAse 1 at a final concentration of 10 U/µg of DNA was added and the mixture was incubated at 37° C. for 18 hours in the presence of 5 mM of $MgCl_2$. An aliquot of the untreated DNA solution was kept as a positive control. The DNAse-treated preparation was found completely devoid of EMS emission at any dilution. Treatment of the DNA solution by a restriction enzyme acting at many sites did not suppress the production of EMS, suggesting that this emission was linked to rather short sequences or was associated with rare sequences.

Nature of the DNA Sequences at the Origin of the EMS:

It is believed that the DNA able to generate EMS suggests that this DNA is associated with pathogenicity in humans and other animals. By contrast, good viruses are probably negative for EMS emission. This suggested that only some sequences of DNA were at the origin of the EMS, since pathogenicity was often associated with the capacity of the microorganism to bind eukaryotic cells, particularly mucosal cells. The disclosed methods and compositions can be used either manually by a technician in a laboratory or can be combined into an automatic analyzer of blood, body fluids, tissue and cells from people and, animals in general, to detect a reservoir virus infection in subjects not showing a viral load. Automatic analysis of samples from people by a laboratory machine is contemplated by this disclosure. Additionally, it is contemplated that a scanner could be used to detect a viral infection by a non-invasive technique (e.g., placing a palm or finger on a scanner plate) to detect the EMS emitted by an EMS generating entity associated with that disease. Although, the HIV virus has been used to demonstrate the production of EMS from pathogenic viruses, other pathogenic viruses (e.g., influences and HPV) can be used with the disclosed methods, compositions and apparatuses. Other embodiments of the invention include:

A method for detecting electromagnetic waves derived from a polynucleotide, such as viral DNA, comprising: extracting and purifying nucleic acids from a sample; diluting the extracted purified nucleic acids in an aqueous solvent; measuring a low frequency electromagnetic emission over time from the diluted extracted purified nucleic acids in an aqueous solvent; performing a signal analysis of the low frequency electromagnetic emission over time; and producing an output, based on the signal analysis, in dependence on the DNA in the sample. Advantageously, this method involves one in which the output varies in dependence on DNA in the sample derived from a pathogenic virus in plasma of a patient suffering from a chronic disease. The viral DNA may be extracted from a biological or physiological sample including tissue, cells, blood, feces, urine, saliva, tears, seminal fluid, sweat, vaginal fluids of a subject, particularly of a subject having or suspected of having a viral infection. The sample may also be extracted from a source external to the subject such as from food or potable water or from an environmental sample. In some embodiments, a DNA sample will be extracted from a sample that has been previously stored, lyophilized, or frozen and stored at a temperature between about −20° C. and −70° C.

The polynucleotide, preferably DNA, may be extracted and purified by diluting the sample with an aqueous buffer and mixing; degrading protein in the diluted sample; precipitating DNA from the buffer solution; and resuspending the precipitated DNA in an aqueous solution. This method may further comprise filtering the resuspended DNA through at least one submicron filter, wherein the sample measured comprises the filtrate. The sample may be made by diluting the filtrate in an aqueous solution prior to measuring, for example, dilution of a resuspended DNA to a concentration of $10^{-2}$ to $10^{-20}$ of its concentration prior to measurement.

The measuring in such a method may comprise placing the diluted extracted purified nucleic acids near an antenna adapted to receive electromagnetic signals having a frequency approaching about 0 Hz, 1, 2, 3, 4, 5, 6, 7, 8, 9, 10, 11, 12, 13, 14, 15, 16, 17, 18, 19 kHz and up to and including 20 kHz, and receiving the electromagnetic signals from the antenna.

The method as described above may employ signal analysis which comprises performing a time domain to frequency domain transformation on the signal and which may further comprise comparing frequency domain transformed signals from two different samples. Signal analysis may also be performed by applying a threshold function to the frequency domain transformed signal. Such signal analysis can be implemented on a general purpose computer and said output is presented through a graphic user interface. Signal analysis may comprise, be determined as, or be displayed as three-dimensional histogram. Background noise reduction may be performed as a part of the signal analysis.

The signal analysis preferably comprises analysis of signal components having frequencies between about 1-20,000 Hz and/or employs a diluting step which dilutes the polynucleotide, such as DNA, to about $10^{-7}$ to $10^{-13}$ of its original concentration.

Another embodiment of the invention is a composition comprising a filtered, vortexed, diluted sample of a polynucleotide, such as DNA, preferably DNA from a pathogenic virus such as a HIV, wherein the filtered, vortexed, diluted sample of DNA has a detectable electromagnetic signal.

The invention also involves a method of detecting an animal having an infection by a pathogen or pathogenic particle comprising placing a body part of an animals on an EMS detecting device, measuring the EMS from the body part, analyzing the EMS, and determining if the EMS corresponds to an EMS produced by a pathogenic particle.

Alternatively, a pathogenic infection in an animal may be detected by a process comprising a) obtaining a body fluid from an animal, b) filtering the body fluid to obtain a filtered body fluid, c) vortexing the filtered body fluid, d) diluting the filtered body fluid in step b) by a factor of at least 1:9, preferably diluting the sample at a dilution of 1:9, e) measuring an EMS from the diluted body fluid in step d), f) analyzing the EMS, and g) determining if the EMS corresponds to an EMS produced by a pathogenic particle. In such a method steps c) and d) are repeated at least one time, twice or more than two times.

The invention in another aspect involves a method of detecting an animal with a pathogenic infection comprising the steps of: a) obtaining a body fluid from an animal, b) filtering the body fluid to obtain a filtered body fluid, c) serial diluting of the filtered body fluid until obtaining a dilution to test for EMS; wherein, the serial diluting comprises multiple cycles of: vortexing the filtered body fluid and diluting the filtered body fluid by a factor of at least 1:9, preferably diluting the sample at a dilution of 1:9; d) measuring an EMS from the diluted body fluid in step d), e) analyzing the EMS, f) determining if the EMS corresponds to an EMS produced by a pathogenic particle.

A method of detecting an animal with a pathogenic infection comprising the steps of: a) obtaining a sample of tissue from an animal, b) extracting DNA from the sample of tissue from the animal, c) making a solution containing the DNA from the sample of tissue from the animal, d)

filtering the solution in step c), e) vortexing the solution in step d), f) diluting the solution in step e) by a factor of at least 1:9, preferably diluting the sample at a dilution of 1:9, g) measuring an EMS from the solution in step f), h) analyzing the EMS, and i) determining if the EMS corresponds to an EMS produced by a pathogenic particle. This method may comprise repeating steps e) and f) at least one time or more than twice.

A method of detecting an animal with a pathogenic infection comprising the steps of: a) obtaining a sample of tissue from an animal, b) extracting DNA from the sample of tissue from the animal, c) making a solution containing the DNA from the sample of tissue from the animal, d) filtering the solution in step c), e) serial diluting of the solution in step c) wherein, the serial diluting comprises multiple cycles of: vortexing the filtered body fluid and diluting the filtered body fluid by a factor of at least 1:9, preferably diluting the sample at a dilution of 1:9; g) measuring an EMS from the solution in step f), h) analyzing the EMS, and i) determining if the EMS corresponds to an EMS produced by a pathogenic particle.

A method of detecting an animal with a pathogenic infection comprising the steps of: a) obtaining a sample of cells from an animal, b) extracting DNA from the sample of cells from the animal, c) making a solution containing the DNA from the sample of cells from the animal, d) filtering the solution in step c), e) vortexing the solution in step d), f) diluting the solution in step e) by a factor of at least 1:9, preferably diluting the sample at a dilution of 1:9, g) measuring an EMS from the solution in step f), h) analyzing the EMS, i) determining if the EMS corresponds to an EMS produced by a pathogenic particle. This method may comprise repeating steps e) and f) at least one time, twice or more than twice.

A method of detecting an animal with a pathogenic infection comprising the steps of: a) obtaining a sample of cells from an animal, b) extracting DNA from the sample of cells from the animal, c) making a solution containing the DNA from the sample of cells from the animal, d) filtering the solution in step c), e) serial diluting of the solution in step d) wherein, the serial diluting comprises multiple cycles of: vortexing the filtered body fluid and diluting the filtered body fluid by a factor of at least 1:9, preferably diluting the sample at a dilution of 1:9; f) measuring an EMS from the solution in step f), g) analyzing the EMS, and h) determining if the EMS corresponds to an EMS produced by a pathogenic particle.

A method of increasing the sensitivity of PCR comprising the steps of: a) obtaining a sample to be analyzed by PCR, b) filtering the sample, c) vortexing the sample, d) diluting the sample by a factor of at least 1:9, preferably diluting the sample at a dilution of 1:9, e) analyzing diluted sample with PCR. This method may involve repeating steps c) and d) at least one time or more than twice.

A method of increasing the sensitivity of PCR comprising the steps of: a) obtaining a sample to be analyzed by PCR, b) filtering the sample, c) serial diluting of the sample until obtaining a dilution to test for EMS; wherein, the serial diluting comprises multiple cycles of: vortexing the filtered body fluid and diluting the filtered body fluid at a dilution of at least 1:9, preferably diluting the sample at a dilution of 1:9; d) diluting the sample at a dilution of at least 1:9, preferably diluting the sample at a dilution of 1:9, and e) analyzing diluted sample with PCR.

A method to increase the sensitivity of PCR to detect HIV comprising: obtaining a sample from an animal, filtering the sample, treating filtered sample with an RNAse, vortexing the sample, diluting the sample by a factor of at least 1:9, preferably diluting the sample at a dilution of 1:9, and analyzing diluted sample with PCR, nested-PCR, RT-PCR, or nested-RT-PCR; or combinations thereof. The steps of vortexing and diluting may be performed once, twice or repeated more than twice.

A method to increase the sensitivity of PCR to detect HIV comprising: obtaining a sample from an animal, filtering the sample, treating the filtered sample with an RNAse; serial diluting of the filtered sample body fluid until obtaining a dilution to test for EMS; wherein, the serial diluting comprises multiple cycles of: vortexing the filtered body fluid and diluting the filtered body fluid by a factor of at least 1:9, preferably diluting the sample at a dilution of 1:9; vortexing the sample, diluting the sample by a factor of at least 1:9, preferably diluting the sample at a dilution of 1:9, and analyzing diluted sample with PCR, nested-PCR, RT-PCR, or nested-RT-PCR; or combinations thereof.

A method to detect reservoir HIV virus comprising: obtaining a sample of body fluid from an animal, filtering the sample, vortexing the sample, diluting the sample at a dilution of at least 1:9, preferably diluting the sample at a dilution of 1:9, measuring an EMS from the diluted sample, analyzing the EMS, and determining if the EMS corresponds to HIV virus. The steps of vortexing and diluting may be performed once, twice or repeated more than twice.

A method to detect reservoir HIV virus comprising: obtaining a sample of body fluid from an animal, filtering the sample, serial diluting of the sample until obtaining a dilution to test for EMS; wherein, the serial diluting comprises multiple cycles of: vortexing the filtered body fluid and diluting the filtered body fluid by a factor of at least 1:9, preferably diluting the sample at a dilution of 1:9; measuring an EMS from the diluted sample, analyzing the EMS, and determining if the EMS corresponds to HIV virus.

A method to detect reservoir HIV virus comprising: obtaining a sample of body fluid from an animal, filtering the sample, treating filtered sample with an RNase, vortexing the sample, diluting the sample by a factor of at least 1:9, preferably diluting the sample at a dilution of 1:9, and analyzing diluted sample with RT-PCR. The steps of vortexing and diluting may be performed once, twice or repeated more than twice.

A method to detect reservoir HIV virus comprising: obtaining a sample of body fluid from an animal, filtering the sample, treating filtered sample with an RNAse, serial diluting of the filtered sample with the RNase body until obtaining a dilution to test for EMS; wherein, the serial diluting comprises multiple cycles of: vortexing the filtered body fluid and diluting the filtered body fluid by a factor of at least 1:9, preferably diluting the sample at a dilution of 1:9; analyzing diluted sample with RT-PCR.

A method to detect reservoir HIV virus comprising: obtaining a sample of body fluid from an animal, filtering the sample, treating filtered sample vortexing the sample, diluting the sample by a factor of at least 1:9, preferably diluting the sample at a dilution of 1:9, and analyzing diluted sample using HIV primers with nested PCR. In this method the steps of vortexing and diluting can be performed once, twice or are repeated more than twice.

A method to detect reservoir HIV virus comprising: obtaining a sample of body fluid from an animal, filtering the sample, treating filtered sample, serial diluting of the filtered sample until obtaining a dilution to test for EMS; wherein, the serial diluting comprises multiple cycles of: vortexing the filtered body fluid and diluting the filtered body fluid at a dilution of at least 1:9, preferably diluting the sample at a dilution of 1:9; analyzing diluted sample using HIV primers with nested PCR.

An apparatus to analyze a sample for a pathogenic infection comprising: a sample loading device; a sample filtering device; a sample diluting device; a sample vortexing device; a sample measuring device for EMS; an EMS analyzer; and a data display device.

An apparatus to analyze an animal for a pathogenic infection comprising: a surface for placing a body part; a measuring device for EMS; an EMS analyzer; and a data display device.

An apparatus to analyze cells for a pathogenic infection comprising: a sample loading device; a sample DNA extraction device; a sample filtering device; a sample diluting device; a sample vortexing device; a sample measuring device for EMS; an EMS analyzer; and a data display device.

In another aspect, the invention encompasses an apparatus to analyze a tissue for a pathogenic infection comprising: a sample loading device; a sample DNA extraction device; a sample filtering device; a sample diluting device; a sample vortexing device; a sample measuring device for EMS; an EMS analyzer; and a data display device.

Another facet of the invention is a method to determine efficiency of a treatment for a pathogenic infection in a person comprising: measuring an EMS in a person corresponding to an EMS from a pathogenic particle; treating the person with a treatment for which an efficiency is being determined; measuring an EMS in the person treated with the treatment; and determining the relationship between the EMS before treatment and the EMS after treatment.

Yet another aspect of the invention is a method to determine a cure of an HIV infection in a person comprising: measuring an EMS in a person corresponding to an EMS from a HIV virus; treating the person with a treatment for which a cure is expected; and not detecting an EMS in the person corresponding to the EMS from the HIV virus.

The invention also relates to a method to treat HIV comprising: measuring an EMS in a person corresponding to an EMS-generating particle from a HIV virus; treating the person with a treatment to eliminate the EMS-generating particle from the HIV virus.

A method to decrease an EMS from an EMS emitting sample comprising: placing an EMS emitting sample next to a non-EMS emitting sample, and waiting an effective amount of time to decrease the EMS in the EMS emitting sample.

A method to induce an EMS in a sample not emitting an EMS comprising: placing an EMS emitting sample next to a vial containing a fluid, and waiting an effective amount of time to induce an EMS in the vial containing the fluid.

A method of detecting viral DNA in a patient with undetectable viral RNA comprising: obtaining a sample of body fluid from a patient, filtering the sample, treating filtered sample with an RNase, vortexing the sample, diluting the sample by a factor of at least 1:9, preferably diluting the sample at a dilution of 1:9, and analyzing diluted sample with RT-PCR. This method may employ the steps of vortexing and diluting being performed once, twice, or more than twice.

A method of detecting viral DNA in a patient with undetectable viral RNA comprising: obtaining a sample of body fluid from a patient, filtering the sample, treating filtered sample with an RNase, serial diluting of the filtered sample with the RNase until obtaining a dilution to test for EMS; wherein, the serial diluting comprises multiple cycles of: vortexing the filtered body fluid and diluting the filtered body fluid at a dilution of a least 1:9, preferably diluting the sample at a dilution of 1:9; and analyzing diluted sample with RT-PCR.

A method to assess the eradication of a viral infection by reduction of viral DNA comprising: measuring an EMS in a person corresponding to an EMS from a viral DNA; treating the person with a treatment for which an efficiency is being determined; measuring an EMS in the person treated with the treatment; and determining the relationship between the EMS before treatment and the EMS after treatment. This method may be applied to subjects having viral infections caused by a HIV, Influenza virus, or other viruses, especially persistent viruses.

A method to confirm or detect an EMS generated by a HIV virus comprising: obtaining a sample from a patient, filtering the sample, treating filtered sample with an RNase, vortexing the sample, diluting the sample by a factor of at least 1:9, preferably diluting the sample at a dilution of 1:9, and amplifying the diluted sample with RT-PCR using a PCR primer for a HIV gene sequence. This method may be performed using a PCR primer for LTR, Gag, Env, Tat, Rev, Nef, Vif, Vpr, Vpu, Pol, and/or for double LTR.

The invention also is directed to a method to confirm or detect an EMS generated by a HIV virus comprising: obtaining a sample from a patient, filtering the sample, treating filtered sample with an RNase, serial diluting of the filtered sample with the RNase until obtaining a dilution to test for EMS; wherein, the serial diluting comprises multiple cycles of: vortexing the filtered body fluid and diluting the filtered body fluid by a factor or at least 1:9, preferably diluting the sample at a dilution of 1:9; and amplifying the diluted sample with RT-PCR using a PCR primer for a HIV gene sequence. This method also includes one in which the PCR primer is for LTR, Gag, Env, Tat, Rev, Nef, Vif, Vpr, Vpu, Pol and/or is for double LTR.

Additional Embodiments of the Disclosed Method and Disclosed Composition

Time Period of Vortexing

In one set of embodiments of the disclosed method or composition or apparatus, the time period of vortexing is at least 1, or at least 2, or at least 3, or at least 4, or at least 5, or at least 6, or at least 7, or at least 8, or at least 9, or at least 10, or at least 11, or at least 12, or at least 13, or at least 14, or at least 15, or at least 16, or at least 17, or at least 18, or at least 19, or at least 20, or at least 25, or at least 30, or at least 35, or at least 40, or at least 45, or at least 50, or at least 55, or at least 60, or at least 90, or at least 120, or at least 150, or at least 180 seconds, or at least 5 minutes, or at least 10 minutes. In another embodiments of the disclosed method the time period of vortexing is more than 1, or more than 2, or more than 3, or more than 4, more than 5, or more than 6, or more than 7, or more than 8, or more than 9, or more than 10, or more than 11, or more than 12, or more than 13, or more than 14, or more than 15, or more than 16, or more than 17, or more than 18, or more than 19, or more than 20, or more than 25, or more than 30, or more than 35, or more than 40, or more than 45, or more than 50, or more than 55, or more than 60, or more than 90, or more than 120, or more than 150, or more than 180 seconds, or more than 5 minutes, or more than 10 minutes, or approximately 1 or approximately 2, or approximately 3, or approximately 4, or approximately 5, or approximately 6, or approximately 7, or approximately 8, or approximately 9, or approximately 10, or approximately 11, or approximately 12, or approximately 13, or approximately 14, or approximately 15, or approximately 16, or approximately 17 seconds, or approximately 18, or approximately 19, or approximately 20, or approximately 25, or approximately 30, or approximately 35, or approximately 40, or approximately 45, or approximately 50, or approximately 55, or approximately 60, or approximately 90, or approximately 120, or approximately 150, or approximately 180 seconds, or approximately 5 minutes, or approximately 10 minutes, or 1, or 2, or 3, or 4, or 5, or 6, or 7, or 8, or 9, or 10, or 11, or 12, or 13, or 14, or 15, or 16, or 17, or 18, or 19, or 20, or 25, or 30, or 35, or 40, or 45, or 50, or 55, or 60, or 90, or 120, or 150, or 180 seconds, or 5 minutes, or 10 minutes.

Filtration, Dilution and Vortex Steps

In one embodiment of the disclosed method or composition or apparatus, the sample is diluted. In one embodiment of the disclosed method the sample is serially diluted. In one embodiment of the disclosed method the sample is diluted in series with the same dilution factor. In one embodiment of the disclosed method the sample is diluted in series with different dilution factors. In one embodiment of the disclosed method the sample is diluted and then vortexed. In one embodiment of the disclosed method the sample is vortexed and then diluted.

In one set of embodiments of the disclosed method or composition or apparatus, the sample is filtered, diluted and vortexed, in that order. In one embodiment of the disclosed method the sample is filtered, diluted and vortexed, and these steps are repeated twice, or three (3) times, or four (4) times, or five (5) times, or six (6) times, or seven (7) times, or eight (8) times, or nine (9) times, or ten (10) times, or eleven (11) times, or twelve (12) times, or thirteen (13) times, or fourteen (14) times, or fifteen (15) times, or sixteen (16) times, or seventeen (17) times, or eighteen (18) times, or nineteen (19) times, or twenty (20) times. In another set of embodiments of the disclosed method the sample is filtered, diluted and vortexed, in that order. In one embodiment of the disclosed method the sample is filtered, diluted and vortexed, and these steps are repeated at least twice, or at least three (3) times, or at least four (4) times, or at least five (5) times, or at least six (6) times, or at least seven (7) times, or at least eight (8) times, or at least nine (9) times, or at least ten (10) times, or at least eleven (11) times, or at least twelve (12) times, or at least thirteen (13) times, or at least fourteen (14) times, or at least fifteen (15) times, or at least sixteen (16) times, or at least seventeen (17) times, or at least eighteen (18) times, or at least nineteen (19) times, or at least twenty (20) times. In a further set of embodiments of the disclosed method the sample is filtered, diluted and vortexed, in that order. In one embodiment of the disclosed method the sample is filtered, diluted and vortexed, and these steps are repeated more than twice, or three (3) times, or four (4) times, or five (5) times, or six (6) times, or seven (7) times, or eight (8) times, or nine (9) times, or ten (10) times, or eleven (11) times, or twelve (12) times, or thirteen (13) times, or fourteen (14) times, or fifteen (15) times, or sixteen (16) times, or seventeen (17) times, or eighteen (18) times, or nineteen (19) times, or twenty (20) times. In a still further set of embodiments of the disclosed method the sample is filtered, diluted and vortexed, in that order. In one embodiment of the disclosed method the sample is filtered, diluted and vortexed, and the "diluted and vortexed" steps are repeated twice, or three (3) times, or four (4) times, or five (5) times, or six (6) times, or seven (7) times, or eight (8) times, or nine (9) times, or ten (10) times, or eleven (11) times, or twelve (12) times, or thirteen (13) times, or fourteen (14) times, or fifteen (15) times, or sixteen (16) times, or seventeen (17) times, or eighteen (18) times, or nineteen (19) times, or twenty (20) times. In another set of embodiments of the disclosed method the sample is filtered, diluted and vortexed, in that order. In one embodiment of the disclosed method the sample is filtered, diluted and vortexed, and the "diluted and vortexed" steps are repeated at least twice, or at least three (3) times, or at least four (4) times, or at least five (5) times, or at least six (6) times, or at least seven (7) times, or at least eight (8) times, or at least nine (9) times, or at least ten (10) times, or at least eleven (11) times, or at least twelve (12) times, or at least thirteen (13) times, or at least fourteen (14) times, or at least fifteen (15) times, or at least sixteen (16) times, or at least seventeen (17) times, or at least eighteen (18) times, or at least nineteen (19) times, or at least twenty (20) times. In a further set of embodiments of the disclosed method the sample is filtered, diluted and vortexed, in that order. In one embodiment of the disclosed method the sample is filtered, diluted and vortexed, and the "diluted and vortexed" steps are repeated more than twice, or more than three (3) times, or more than four (4) times, or more than five (5) times, or more than six (6) times, or more than seven (7) times, or more than eight (8) times, or more than nine (9) times, or more than ten (10) times, or more than eleven (11) times, or more than twelve (12) times, or more than thirteen (13) times, or more than fourteen (14) times, or more than fifteen (15) times, or more than sixteen (16) times, or more than seventeen (17) times, or more than eighteen (18) times, or more than nineteen (19) times, or more than twenty (20) times.

Filtration, Vortex and Dilution Steps

In one set of embodiments of the disclosed method or composition or apparatus, the sample is filtered, vortexed and diluted, in that order, which may be repeated twice, or three (3) times, or four (4) times, or five (5) times, or six (6) times, or seven (7) times, or eight (8) times, or nine (9) times, or ten (10) times, or eleven (11) times, or twelve (12) times, or thirteen (13) times, or fourteen (14) times, or fifteen (15) times, or sixteen (16) times, or seventeen (17) times, or eighteen (18) times, or nineteen (19) times, or twenty (20) times. In another set of embodiments of the disclosed method the sample is filtered, vortexed and diluted, in that order. In one embodiment of the disclosed method the sample is filtered, vortexed and diluted, and these steps are repeated at least twice, or at least three (3) times, or at least four (4) times, or at least five (5) times, or at least six (6) times, or at least seven (7) times, or at least eight (8) times, or at least nine (9) times, or at least ten (10) times, or at least eleven (11) times, or at least twelve (12) times, or at least thirteen (13) times, or at least fourteen (14) times, or at least fifteen (15) times, or at least sixteen (16) times, or at least seventeen (17) times, or at least eighteen (18) times, or at least nineteen (19) times, or at least twenty (20) times, or more than twice, or more than three (3) times, or more than four (4) times, or more than five (5) times, or more than six (6) times, or more than seven (7) times, or more than eight (8) times, or more than nine (9) times, or more than ten (10) times, or more than eleven (11) times, or more than twelve (12) times, or more than thirteen (13) times, or more than fourteen (14) times, or more than fifteen (15) times, or more than sixteen (16) times, or more than seventeen (17) times, or more than eighteen (18) times, or more than nineteen (19) times, or more than twenty (20) times, or.

In another set of embodiments of the disclosed method or composition or apparatus, the sample is filtered, vortexed and diluted, in that order. In one embodiment of the disclosed method the sample is filtered, vortexed and diluted, and the "vortexed and diluted" steps are repeated twice, or three (3) times, or four (4) times, or five (5) times, or six (6)

times, or seven (7) times, or eight (8) times, or nine (9) times, or ten (10) times, or eleven (11) times, or twelve (12) times, or thirteen (13) times, or fourteen (14) times, or fifteen (15) times, or sixteen (16) times, or seventeen (17) times, or eighteen (18) times, or nineteen (19) times, or twenty (20) times, or at least twice, or at least three (3) times, or at least four (4) times, or at least five (5) times, or at least six (6) times, or at least seven (7) times, or at least eight (8) times, or at least nine (9) times, or at least ten (10) times, or at least eleven (11) times, or at least twelve (12) times, or at least thirteen (13) times, or at least fourteen (14) times, or at least fifteen (15) times, or at least sixteen (16) times, or at least seventeen (17) times, or at least eighteen (18) times, or at least nineteen (19) times, or at least twenty (20) times, or more than twice, or more than three (3) times, or more than four (4) times, or more than five (5) times, or more than six (6) times, or more than seven (7) times, or more than eight (8) times, or more than nine (9) times, or more than ten (10) times, or more than eleven (11) times, or more than twelve (12) times, or more than thirteen (13) times, or more than fourteen (14) times, or more than fifteen (15) times, or more than sixteen (16) times, or more than seventeen (17) times, or more than eighteen (18) times, or more than nineteen (19) times, or more than twenty (20) times.

Dilution Step

In one embodiment of the disclosed method or composition or apparatus, the EMS is measured in a sample diluted $10^{-1}$, or $10^{-2}$, or $10^{-3}$, or $10^{-4}$, or $10^{-5}$, or $10^{-6}$, or $10^{-7}$, or $10^{-8}$, or $10^{-9}$, or $10^{-10}$, or $10^{-11}$, or $10^{-12}$, or $10^{-13}$, or $10^{-14}$, or $10^{-15}$, or $10^{-16}$, or $10^{-17}$, or $10^{-18}$, or $10^{-19}$, or $10^{-20}$. In another embodiment of the disclosed method the EMS is measured in a sample diluted at least $10^{-1}$, or at least $10^{-2}$, or at least $10^{-3}$, or at least $10^{-4}$ n, or at least $10^{-5}$, or at least $10^{-6}$, or at least $10^{-7}$, or at least $10^{-8}$, or at least $10^{-9}$, or at least $10^{-10}$, or at least $10^{-11}$, or at least $10^{-12}$, or at least $10^{-13}$, or at least $10^{-14}$, or at least $10^{-15}$, or at least $10^{-16}$, or at least $10^{-17}$, or at least $10^{-18}$, or at least $10^{-19}$, or at least $10^{-20}$. In a further embodiment of the disclosed method the EMS is measured in a sample diluted more than $10^{-1}$, or more than $10^{-2}$, or more than $10^{-3}$, or more than $10^{-4}$, or more than $10^{-5}$, or more than $10^{-6}$, or more than $10^{-7}$ in, or more than $10^{-8}$, or more than $10^{-9}$, or more than $10^{-10}$, or more than $10^{-11}$, or more than $10^{-12}$, or more than $10^{-13}$, or more than $10^{-14}$, or more than $10^{-15}$, or more than $10^{-16}$, or more than $10^{-17}$, or more than $10^{-18}$, or more than $10^{-19}$, or more than $10^{-20}$. In a still further embodiment of the disclosed method the EMS is measured in a sample diluted approximately $10^{-1}$, or approximately $10^{-2}$, or approximately $10^{-3}$, or approximately $10^{-4}$, or approximately $10^{-5}$, or approximately $10^{-6}$, or approximately $10^{-7}$, or approximately $10^{-8}$, or approximately $10^{-9}$, or approximately $10^{-10}$, or approximately $10^{-11}$, or approximately $10^{-12}$, or approximately $10^{-13}$, or approximately $10^{-14}$, or approximately $10^{-15}$, or approximately $10^{-16}$, or approximately $10^{-17}$, or approximately $10^{-18}$, or approximately $10^{-19}$, or approximately $10^{-20}$.

Dilution Factor

In one set of embodiments of the disclosed method or composition or apparatus, the dilution factor is 1:1, or 1:2, or 1:3, or 1:4, or 1:5, or 1:6, or 1:7, or 1:8, or 1:9, preferably diluting the sample at a dilution of 1:9, or 1:10, or 1:11, or 1:12, or 1:13, or 1:14, or 1:15, or 1:16, or 1:17, or 1:18, or 1:19, or 1:20, or 1:25, or 1:30, or 1:35, or 1:40, or 1:45, or 1:50, or 1:55, or 1:60, or 1:65, or 1:70, or 1:75, or 1:80, or 1:85, or 1:90, or 1:95, or 1:100, or at least 1:1, or at least 1:2, or at least 1:3, or at least 1:4, or at least 1:5, or at least 1:6, or at least 1:7, or at least 1:8, or at least 1:9, or at least 1:10, or at least 1:11, or at least 1:12, or at least 1:13, or at least 1:14, or at least 1:15, or at least 1:16, or at least 1:17, or at least 1:18, or at least 1:19, or at least 1:20, or at least 1:25, or at least 1:30, or at least 1:35, or at least 1:40, or at least 1:45, or at least 1:50, or at least 1:55, or at least 1:60, or at least 1:65, or at least 1:70, or at least 1:75, or at least 1:80, or at least 1:85, or at least 1:90, or at least 1:95, or at least 1:100, or more than 1:1, or more than 1:2, or more than 1:3, or more than 1:4, or more than 1:5, or more than 1:6, or more than 1:7, or more than 1:8, or more than 1:9, or more than 1:10, or more than 1:11, or more than 1:12, or more than 1:13, or more than 1:14, or more than 1:15, or more than 1:16, or more than 1:17, or more than 1:18, or more than 1:19, or more than 1:20, or more than 1:25, or more than 1:30, or more than 1:35, or more than 1:40, or more than 1:45, or more than 1:50, or more than 1:55, or more than 1:60, or more than 1:65, or more than 1:70, or more than 1:75, or more than 1:80, or more than 1:85, or more than 1:90, or more than 1:95, or more than 1:100, or approximately 1:1, or approximately 1:2, or approximately 1:3, or approximately 1:4, or approximately 1:5, or approximately 1:6, or approximately 1:7, or approximately 1:8, or approximately 1:9, preferably diluting the sample at a dilution of 1:9, or approximately 1:10, or approximately 1:11, or approximately 1:12, or approximately 1:13, or approximately 1:14, or approximately 1:15, or approximately 1:16, or approximately 1:17, or approximately 1:18, or approximately 1:19, or approximately 1:20, or approximately 1:25, or approximately 1:30, or approximately 1:35, or approximately 1:40, or approximately 1:45, or approximately 1:50, or approximately 1:55, or approximately 1:60, or approximately 1:65, or approximately 1:70, or approximately 1:75, or approximately 1:80, or approximately 1:85, or approximately 1:90, or approximately 1:95, or approximately 1:100.

Sample Preparation

In one embodiment of the disclosed method or composition or apparatus, the sample is unfrozen. In one embodiment of the disclosed method the sample is frozen and then the DNA is extracted from the sample. In one embodiment of the disclosed method the sample is unfrozen and the DNA is extracted from the sample.

Sample Material

In one embodiment of the disclosed method or composition or apparatus, the sample is a body fluid. In one embodiment of the disclosed method the sample is blood, or plasma, or urine, or sweat, or tears, or *salvia*, or seminal fluid, or vaginal fluid, or feces, or fecal cells.

In one embodiment of the disclosed method or composition or apparatus the sample is a tissue, or a cell, or a combination of tissue and cells, or cells, or red blood cells, or white blood cells, or lymphocytes, or platelets, or cells that centrifuge with red blood cells, or skin, or buccal cells, or nasal cells, or hair follicles, or ectoderm cells, or endoderm cells, or mesoderm cells, or sperm, or oocytes, or eggs, or gametocytes, or stem cells, or cloned cells, or derived cells.

In one embodiment of the disclosed method or composition or apparatus the sample is body part. In one embodiment of the disclosed method the sample is a hand, or a finger, or an eye, or a hair, or a foot, or a toe, or a face, or a palm, or a mouth, or a cheek, or a lip, or an arm, or a leg.

Sample Solution Content

In one embodiment of the disclosed method or composition or apparatus the sample is filtered. In one embodiment of the disclosed method the sample is a solution containing DNA and the solution is filtered. In one embodiment of the disclosed method the sample is a solution containing RNA and the solution is filtered.

In one set of embodiments of the disclosed method or composition or apparatus the sample is a solution containing DNA and/or RNA, and the solution is filtered with a filter of at least 100 nm porosity, or at least 95 nm porosity, or at least 90 nm porosity, at least 85 nm porosity, or at least 80 nm porosity, or at least 75 nm porosity, or at least 70 nm porosity, or at least 65 nm porosity, or at least 60 nm porosity, or at least 55 nm porosity, or at least 50 nm porosity, or at least 45 nm porosity, or at least 40 nm porosity, or at least 35 nm porosity, or at least 30 nm porosity, or at least 25 nm porosity, or at least 20 nm porosity, or at least 15 nm porosity, or at least 10 nm porosity, or at least 5 nm porosity. In one embodiment of the disclosed composition the sample is a solution containing DNA and/or RNA, and the solution is filtered with a filter of approximately 100 nm porosity, 100 nm porosity, or approximately 95 nm porosity, or approximately 90 nm porosity, or approximately 85 nm porosity, or approximately 80 nm porosity, or approximately 75 nm porosity, or approximately 70 nm porosity, or approximately 65 nm porosity, or approximately 60 nm porosity, or approximately 55 nm porosity, or approximately 50 nm porosity, or approximately 45 nm porosity, or approximately 40 nm porosity, or approximately 35 nm porosity, or approximately 30 nm porosity, or approximately 25 nm porosity, or approximately 20 nm porosity, or approximately 15 nm porosity, or approximately 10 nm porosity, or approximately 5 nm porosity.

In one embodiment of the disclosed composition the solution comprises particles not greater than 100 nm, or not greater than 95 nm, or not greater than 90 nm, or not greater than 85 nm, or not greater than 80 nm, or not greater than 75 nm, or not greater than 70 nm, or not greater than 65 nm, or not greater than 60 nm, or not greater than 55 nm, or not greater than 50 nm, or not greater than 45 nm, or not greater than 40 nm, or not greater than 35 nm, or not greater than 30 nm, or not greater than 25 nm, or not greater than 20 nm, or not greater than 15 nm, or not greater than 10 nm, or not greater than 5 nm, or less than 100 nm, or less than 95 nm, or less than 90 nm, or less than 85 nm, or less than 80 nm, or less than 75 nm, or less than 70 nm, or less than 65 nm, or less than 60 nm, or less than 55 nm, or less than 50 nm, or less than 45 nm, or less than 40 nm, or less than 35 nm, or less than 30 nm, or less than 25 nm, or less than 20 nm, or less than 15 nm, or less than 10 nm, or less than 5 nm. In one embodiment of the disclosed composition the solution comprises particles less than approximately 100 nm, or less than approximately 95 nm, or less than approximately 90 nm, or less than approximately 85 nm, or less than approximately 80 nm, or less than approximately 75 nm, or less than approximately 70 nm, or less than approximately 65 nm, or less than approximately 60 nm, or less than approximately 55 nm, or less than approximately 50 nm, or less than approximately 45 nm, or less than approximately 40 nm, or less than approximately 35 nm, or less than approximately 30 nm, or less than approximately 25 nm, or less than approximately 20 nm, or less than approximately 15 nm, or less than approximately 10 nm, or less than approximately 5 nm.

In one embodiment of the disclosed composition the solution comprises particles not greater than approximately 100 nm, or not greater than approximately 95 nm, or not greater than approximately 90 nm, or not greater than approximately 85 nm, or not greater than approximately 80 nm, or not greater than approximately 75 nm, or not greater than approximately 70 nm, or not greater than approximately 65 nm, or not greater than approximately 60 nm, or not greater than approximately 55 nm, or not greater than approximately 50 nm, or not greater than approximately 45 nm, or not greater than approximately 40 nm, or not greater than approximately 35 nm, or not greater than approximately 30 nm, or not greater than approximately 25 nm, or not greater than approximately 20 nm, or not greater than approximately 15 nm, or not greater than approximately 10 nm, or not greater than approximately 5 nm.

PCR Primers

In one embodiment of the disclosed method or composition or apparatus the sample is analyzed with PCR primers. In one embodiment of the disclosed method the sample is analyzed with a PCR primer of a HIV gene. In one embodiment of the disclosed method the sample is analyzed with a PCR primer of a HIV gene and the HIV gene is Gag. In one embodiment of the disclosed method the sample is analyzed with a PCR primer of a HIV gene and the HIV gene is Pol. In one embodiment of the disclosed method the sample is analyzed with a PCR primer of a HIV gene and the HIV gene is Env. In one embodiment of the disclosed method the sample is analyzed with a PCR primer of a HIV gene and the HIV gene is Tat. In one embodiment of the disclosed method the sample is analyzed with a PCR primer of a HIV gene and the HIV gene is Rev. In one embodiment of the disclosed method the sample is analyzed with a PCR primer of a HIV gene and the HIV gene is Nef. In one embodiment of the disclosed method the sample is analyzed with a PCR primer of a HIV gene and the HIV gene is Vif. In one embodiment of the disclosed method the sample is analyzed with a PCR primer of a HIV gene and the HIV gene is Vpr. In one embodiment of the disclosed method the sample is analyzed with a PCR primer of a HIV gene and the HIV gene is Vpu. In one embodiment of the disclosed method the sample is analyzed with a PCR primer of a HIV sequence and the HIV sequence is LTR. In one embodiment of the disclosed method the sample is analyzed with a PCR primer of a HIV sequence and the HIV sequence is double LTR. In one embodiment of the disclosed method the sample is analyzed with a PCR primer of a HIV gene of a HIV variant. In one embodiment of the disclosed method the sample is analyzed with a PCR primer of at least one HIV gene. In one embodiment of the disclosed method the sample is analyzed with PCR primers of a combination of HIV genes. In one embodiment of the disclosed method the sample is analyzed with a PCR primer of a partial nucleotide sequence of the HIV sequence. In one embodiment of the disclosed method the sample is analyzed with a PCR primer of a nucleotide sequence of the DNA translation of a HIV RNA.

Viruses

In one embodiment of the disclosed method or composition or apparatus, the detected virus is the HIV virus, or the Chickenpox (Varicella) virus, or the Common cold virus, or the Cytomegalovirus, or the Colorado tick fever virus, or the Dengue fever virus, or the Ebola hemorrhagic fever virus, or the Hand, foot and mouth disease virus, or the Hepatitis virus, or the Herpes simplex virus, or the Herpes zoster virus, or the HPV virus, or the Influenza (Flu) virus, or the Lassa fever virus, or the Measles virus, or the Marburg hemorrhagic fever virus, or the Infectious mononucleosis virus, or the Mumps virus, or the Norovirus, or the Poliomyelitis virus, or the Progressive multifocal leukencephalopathy virus, or the Rabies virus, or the Rubella virus, or the SARS virus, or the Smallpox (Variola) virus, or the Viral encephalitis virus, or the Viral gastroenteritis virus, or the Viral meningitis virus, or the Viral pneumonia virus, or the West Nile disease virus, or the Yellow fever virus.

Pathogenic Particle

In one embodiment of the disclosed method or composition or apparatus the pathogenic particle is a fungal cell. In one embodiment of the disclosed method the pathogenic particle is a bacteria. In one embodiment of the disclosed method the pathogenic particle is a virus.

Pathogenic Infection

In one embodiment of the disclosed method or composition or apparatus the pathogenic infection is a fungal infection. In one embodiment of the disclosed method the pathogenic infection is a bacterial infection. In one embodiment of the disclosed method the pathogenic infection is a viral infection.

Particle Size

In one embodiment of the disclosed apparatus the solution comprises particles less than 100 nm, or less than 95 nm, or less than 90 nm, or less than 85 nm, or less than 80 nm, or less than 75 nm, or less than 70 nm, or less than 65 nm, or less than 60 nm, or less than 55 nm, or less than 50 nm, or less than 45 nm, or less than 40 nm, or less than nm, or less than 30 nm, or less than 25 nm, or less than 20 nm, or less than 15 nm, or less than 10 nm, or less than 5 nm, or less than approximately 100 nm, or less than approximately 95 nm, or less than approximately 90 nm, or less than approximately 85 nm, or less than approximately 80 nm, or less than approximately 75 nm, or less than approximately 70 nm, or less than approximately 65 nm, or less than approximately 60 nm, or less than approximately 55 nm, or less than approximately 50 nm, or less than approximately 45 nm, or less than approximately 40 nm, or less than approximately 35 nm, or less than approximately 30 nm, or less than approximately 25 nm, or less than approximately 20 nm, or less than approximately 15 nm, or less than approximately 10 nm, or less than approximately 5 nm, or not greater than 100 nm, or not greater than 95 nm, or not greater than 90 nm, or not greater than 85 nm, or not greater than 80 nm, or not greater than 75 nm, or not greater than 70 nm, or not greater than 65 nm, or not greater than 60 nm, or not greater than 55 nm, or not greater than 50 nm, or not greater than 45 nm, or not greater than 40 nm, or not greater than 35 nm, or not greater than 30 nm, or not greater than 25 nm, or not greater than 20 nm, or not greater than 15 nm, or not greater than 10 nm, or not greater than 5 nm, or not greater than approximately 100 nm, or not greater than approximately 95 nm, or not greater than approximately 90 nm, or not greater than approximately 85 nm, or not greater than approximately 80 nm, or not greater than approximately 75 nm, or not greater than approximately 70 nm, or not greater than approximately 65 nm, or not greater than approximately 60 nm, or not greater than approximately 55 nm, or not greater than approximately 50 nm, or not greater than approximately 45 nm, or not greater than approximately 40 nm, or not greater than approximately 35 nm, or not greater than approximately 30 nm, or not greater than approximately 25 nm, or not greater than approximately 20 nm, or not greater than approximately 15 nm, or not greater than approximately 10 rim, or not greater than approximately 5 nm.

Modifications and Other Embodiments

Various modifications and variations of the described methods, procedures, techniques, and compositions as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the medical, virological, immunological, pharmacological, molecular biological, physical sciences including electronic arts, or related fields are intended to be within the scope of the following claims.

INCORPORATION BY REFERENCE

Each document, patent application or patent publication cited by or referred to in this disclosure is incorporated by reference in its entirety. Any patent document to which this application claims priority is also incorporated by reference in its entirety. Specifically, priority document Provisional Application U.S. 61/186,610, filed Jun. 12, 2009, including all its attachments; Montagnier, et al., Intediscip. Sci. Comput. Life Sci., pp. 1-10 (2009); Montagnier, et al., Electromagnetic detection of HIV DNA in the blood of AIDS patients treated by antiretroviral therapy; and Montagnier, System and Method for the Analysis of DNA sequences in Biological Fluids are hereby incorporated by reference.

What is claimed is:

1. A method for detecting a polynucleotide comprising:
obtaining a clinical specimen from a human, the clinical specimen lacking cellular nuclei;
isolating deoxyribonucleic acids from the clinical specimen;
pretreating the isolated deoxyribonucleic acids with reverse transcriptase;
performing a polymerase chain reaction amplification on at least the reverse transcriptase pretreated isolated deoxyribonucleic acids, using primers specific for at least one gene sequence of HIV selected from the group consisting of LTR, Gag, Env, Tat, Rev, Nef, Vif, Vpr, Vpu, Pol, and double LTR; and
detecting an amplicon corresponding to the at least one gene sequence of HIV.

2. The method according to claim 1, comprising treating the isolated deoxyribonucleic acids from the clinical specimen with RNase, and subsequently treating the RNase-treated clinical specimen with the reverse transcriptase, the RNase and the reverse transcriptase being distinct enzymes.

3. The method according to claim 2, wherein the polymerase chain reaction amplification is performed using Taq polymerase.

4. The method according to claim 1, wherein the at least one gene sequence of HIV comprises HIV DNA LTR, and the amplicon comprises a 104 bp amplicon which differs from HIV DNA LTR by 2 base pairs.

5. The method according to claim 1, wherein the isolated deoxyribonucleic acids from the clinical specimen are derived from a washed red blood cell centrifuge pellet.

6. The method according to claim 1, wherein the at least one primer comprises a primer selective for HIV LTR.

7. The method according to claim 1, wherein the isolated deoxyribonucleic acids from the clinical specimen are derived from blood plasma.

8. The method according to claim 1, wherein the performing a polymerase chain reaction amplification on the clinical specimen comprises performing nested PCR.

9. The method according to claim 1, further comprising sequencing the amplicon.

10. The method according to claim 1, wherein the clinical specimen obtained from a human is subjected to density gradient centrifugation, and the isolated deoxyribonucleic acids are selected from a fraction having a density of between 1.15 and 1.25, excluding a density of 1.16 including HIV virions.

11. A method for detecting a polynucleotide comprising:
   obtaining a specimen from a living organism;
   isolating deoxyribonucleic acids from a non-nuclear portion the specimen;
   treating the isolated deoxyribonucleic acids with reverse transcriptase;
   performing a polymerase chain reaction amplification on the reverse transcriptase treated isolated deoxyribonucleic acids, using primers specific for at least one retroviral pathogen of the living organism; and
   detecting an amplicon selectively associated with the primers,
   wherein a sensitivity of detection of the amplicon from the polymerase chain reaction amplification of the isolated deoxyribonucleic acids selectively associated with the primers is increased by the treatment with reverse transcriptase, as compared to a sensitivity absent the treatment with reverse transcriptase.

12. The method according to claim 11, further comprising, treating the isolated deoxyribonucleic acids from the specimen with RNase, to degrade RNA present in the isolated deoxyribonucleic acids, before treating with reverse transcriptase, wherein the RNase and reverse transcriptase are distinct enzymes.

13. The method according to claim 11, wherein the polymerase chain reaction amplification is performed using Taq polymerase.

14. The method according to claim 11, wherein the amplicon comprises a 104 bp amplicon that differs by no more than 2 bases from HIV DNA LTR.

15. The method according to claim 11, wherein the isolated deoxyribonucleic acids from the clinical specimen are derived from a washed red blood cell centrifuge pellet.

16. The method according to claim 11, wherein the primers comprise at least one pair of primers selective for at least one of LTR, Gag, Env, Tat, Rev, Nef, Vif, Vpr, Vpu, Pol, and double LTR.

17. The method according to claim 11, wherein the primers comprise at least one pair of primers selective for LTR, further comprising sequencing the amplicon.

18. A method of detecting an HIV deoxyribonucleic acid, comprising:
   obtaining a clinical specimen from a human comprising washed red blood cells;
   isolating deoxyribonucleic acids from the clinical specimen;
   treating the isolating deoxyribonucleic acids with a reverse transcriptase, using the isolating deoxyribonucleic acids as a template;
   performing a polymerase chain reaction amplification on the clinical specimen using Taq polymerase, using HIV gene-specific primers; and
   detecting an amplicon which is homologous with a portion of the HIV DNA having a length of at least 104 bp with no more than a 2 bp difference within the DNA having the length of at least 104 bp,
   wherein the reverse transcriptase treatment increases a sensitivity of the detection of the amplicon as compared to the absence of the reverse transcriptase treatment.

19. The method according to claim 18, wherein the amplicon is homologous to a 104 bp sequence of HIV DNA LTR, further comprising verifying a sequence of the amplicon.

* * * * *